United States Patent

Dawson et al.

Patent Number: 4,532,343
Date of Patent: Jul. 30, 1985

[54] AROMATIC RETINOIC ACID ANALOGUES

[75] Inventors: Marcia I. Dawson, Los Altos; Peter D. Hobbs, Woodside, both of Calif.

[73] Assignee: SRI International, Menlo Park, Calif.

[21] Appl. No.: 443,118

[22] Filed: Nov. 19, 1982

[51] Int. Cl.³ .............................................. C07C 69/76
[52] U.S. Cl. ...................................... 514/543; 560/8;
560/65; 562/474; 562/405; 564/170; 564/171; 564/174; 560/64; 514/544; 514/134; 514/617
[58] Field of Search .............. 560/8, 64, 65; 562/474, 562/405; 424/308, 317, 320

[56] References Cited

PUBLICATIONS

Dawson, M. I. et al., J. Med. Chem. 1981, 24, 583–592.

Primary Examiner—Paul J. Killos
Attorney, Agent, or Firm—Ciotti & Murashige

[57] ABSTRACT

Aromatic retinoic acid analogues of the formula

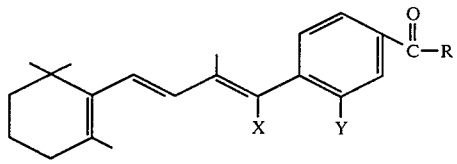

where X is hydrogen or fluorine, Y is hydrogen, halogen of atomic number 9 or 17, hydroxy, alkyl of 1 to 2 carbon atoms or alkoxy of 1 to 2 carbon atoms and R is hydroxy, alkoxy, aroxy, or $NR^1R^2$ where $R^1$ is hydrogen, alkyl, or aryl and $R^2$ is alkyl or aryl, with the proviso that when Y is hydrogen, X is fluorine. These retinoids are useful as chemopreventive agents for inhibiting tumor promotion in epithelial cells and for treating nonmalignant skin disorders.

13 Claims, No Drawings

AROMATIC RETINOIC ACID ANALOGUES

REFERENCE TO GOVERNMENT GRANT OR CONTRACT

The invention described herein was made in the course of work under grant or contract from the National Institute of Health.

DESCRIPTION

1. Technical Field

The invention is in the fields of retinoid chemistry and chemotherapy. More particularly, the invention relates to certain aromatic retinoic acid analogues.

2. Background Art

The progressive loss of the regulation of cellular differentiation by epithelial cells can result in cancer. Retinoic acid and some of its analogues (retinoids) have been investigated as "chemopreventive" agents, that is, agents that interfere with tumor promotion in epithelial cells. Boutwell, et al, *Advances in Enzyme Regulation* V.17, Ed. Weber, G., Pergamon Press (1979); Verma, A. K., et al, *Cancer Res* (1979) 39:419–427; Dawson, M. I., et al, *J Med Chem* (1980) 23:1013–1022 and *J Med Chem* (1981) 24:583–592.

The latter Dawson, M. I., et al, article reports the preparation of (1E, 3E) - and (1Z, 3E)-1-(4-carboxyphenyl)-2-methyl-4-(2,6,6-trimethyl-1-cyclohexen-1-yl)-1,3-butadiene, the methyl and ethyl esters thereof, (E)-1-(2-carboxyphenyl)-4-methyl-6-(2,6,6-trimethyl-1-cyclohexen-1-yl)-1,3,5-hexatriene and the methyl ester thereof, (E)-1-[2-(tetrahydropyranyloxy)phenyl]-4-methyl-6-(2,6,6-trimethyl-1-cyclohexen-1-yl)-1,3,5-hexatriene and the (1E, 3Z, 5E) isomer thereof, and (E)-1-(2-hydroxyphenyl)-4-methyl-6-(2,6,6-trimethyl-1-cyclohexen-1-yl)-1,3,5-hexatriene and its (1E, 3Z, 5E) isomer. Some of these aromatic retinoic acid analogues exhibited biological activity in the ornithine decarboxylase (ODC) assay, which assay is described by Verma, A. K. and Boutwell, R. K., *Cancer Res* (1977) 37:2196–2201.

Pawson, B. A., et al, *J Med Chem* (1979) 22:1059–1067 describes various fluoro-substituted retinoic acids and aromatic retinoates.

A principal object of this invention is to provide new aromatic retinoic acid analogues that are biologically active.

DISCLOSURE OF THE INVENTION

The retinoic acid analogues of the invention are of the formula

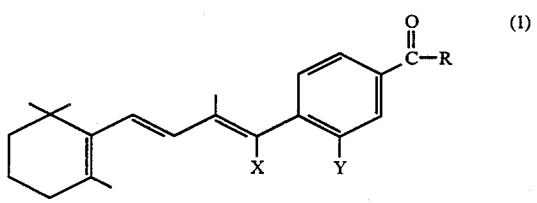

where X is hydrogen or fluorine, Y is hydrogen, halogen of atomic number 9 or 17, hydroxy, alkyl of 1 to 2 carbon atoms, or alkoxy of 1 to 2 carbon atoms and R is hydroxy, alkoxy, aroxy, or $NR^1R^2$ where $R^1$ is hydrogen, alkyl, or aryl and $R^2$ is alkyl or aryl, with the proviso that when Y is hydrogen, X is fluorine.

When used as pharmaceuticals, e.g., as a chemopreventive agent or for treating skin disorders such as proliferative skin diseases or acne, one or more of these retinoids is combined with a suitable pharmaceutically acceptable carrier and an effective dose thereof is administered to the patient.

MODES FOR CARRYING OUT THE INVENTION

The alkoxy groups represented by R will usually contain 1 to about 8 carbon atoms, preferably 1 to 4 carbon atoms, and the aroxy groups represented thereby will usually be mononuclear and contain 6 to 15 carbon atoms, more usually 6 to 10 carbon atoms. Preferred aroxy groups are phenoxy and hydroxy- or $C_1$–$C_4$ alkoxy-monosubstituted phenoxy. The alkoxy groups may be straight chain or branched chain. Examples of such alkoxy groups are methoxy, ethoxy, n-propoxy, i-propoxy, n-butoxy, s-butoxy, t-butoxy, n-pentoxy, n-hexoxy, 2-methylpentoxy, n-heptoxy, 3-methylhexoxy, and n-octoxy. Examples of aroxy groups are phenoxy, o-, m-, p-hydroxyphenoxy o-, m-, p-methoxyphenoxy, toloxy, cumoxy, xyloxy, and naphthoxy.

The alkyl groups represented by $R^1$ and $R^2$ may be straight chain or branched chain. They will typically each contain 1 to 8 carbon atoms, preferably 1 to 4 carbon atoms, and have 0 or 1 hydroxy substituent. Examples of such alkyl groups are methyl, ethyl, propyl, isopropyl, n-butyl, s-butyl, n-amyl, n-hexyl, 2-methylamyl, n-heptyl, 3-methylhexyl, n-octyl, hydroxymethyl, 2-hydroxyethyl, 3-hydroxypropyl, 2-hydroxyhexyl, and the like. The corresponding aryl groups represented by $R^1$ and $R^2$ may be substituted or unsubstituted mononuclear or polynuclear moieties. The substituents will usually be lower (ie, 1 to 4 carbon atoms) alkyl, lower alkoxy, or hydroxy. When substituted, the group will usually be mono-substituted. Examples of such groups are phenyl, o-, m-, or p-hydroxyphenyl, o-, m-, or p-methoxyphenyl, ethylbenzyl, cumyl, naphthyl, phenanthryl, azulyl, and the like. These aryl groups will usually contain 6 to about 15 carbon atoms, more usually 6 to 10 carbon atoms. Phenyl, 4-hydroxyphenyl, and 4-methoxyphenyl are preferred aryl groups Examples of acids (R=OH) represented by formula (1) are: (1Z,3E)-1-(4-carboxyphenyl)-1-fluoro-2-methyl-(2,6,6-trimethyl-1-cyclohexen-1-yl)-1,3-butadiene; (E)-1-(4-carboxy-2-fluorophenyl)-2-methyl-(2,6,6-trimethyl-1-cyclohexen-1-yl)-1,3-butadiene; (1Z,3E)-1-(4-carboxy-2-fluorophenyl)-1-fluoro-2-methyl-(2,6,6-trimethyl-1-cyclohexen-1-yl)-1,3-butadiene; (E)-1-(4-carboxy-2-chlorophenyl)-2-methyl-(2,6,6-trimethyl-1-cyclohexen-1-yl)-1,3-butadiene; (1Z,3E)-1-(4-carboxy-2-chlorophenyl)-1-fluoro-2-methyl-(2,6,6-trimethyl-1-cyclohexen-1-yl)-1,3-butadiene; (E)-1-(4-carboxy-2-methylphenyl)-2-methyl-(2,6,6-trimethyl-1-cyclohexen-1-yl)-1,3-butadiene; (1Z,3E)-1-(4-carboxy-2-methylphenyl)-1-fluoro-2-methyl-(2,6,6-trimethyl-1-cyclohexen-1-yl)-1,3-butadiene; (E)-1-(4-carboxy-2-ethylphenyl)-2-methyl-(2,6,6-trimethyl-1-cyclohexen-1-yl)-1,3-butadiene; (1Z,3E)-1-(4-carboxy-2-ethylphenyl)-1-fluoro-2-enthyl-(2,6,6-trimethyl-1-cyclohexen-1-yl)-1,3-butadiene; (1Z,3E)-1-(4-carboxy-2-ethoxyphenyl)-1-fluoro-2-methyl-(2,6,6-trimethyl-1-cyclohexen-1-yl)-1,3-butadiene; (E)-1-(4-carboxy-2-ethoxyphenyl)-2-methyl-(2,6,6-trimethyl-1-cyclohexen-1-yl)-1,3-butadiene; (E)-1-(4-carboxy-2-hydroxyphenyl)-2-methyl-(2,6,6-trimethyl-1-cyclohexen-1-yl)-1,3-butadiene;

(1Z,3E)-1-(4-carboxy-2-hydroxyphenyl)-1-fluoro-2-methyl-(2,6,6-trimethyl-1-cyclohexen-1-yl)-1,3-butadiene; (E)-1-(4-carboxy-2-methoxyphenyl)-2-methyl-(2,6,6-trimethyl-1-cyclohexen-1-yl)-1,3-butadiene; and (1Z,3E)-1-(4-carboxy-2-methoxyphenyl)-1-fluoro-2-methyl-(2,6,6-trimethyl-1-cyclohexen-1-yl)-1,3-butadiene.

Examples of esters (R=alkoxy, aroxy) represented by formula (1) are: (1Z,3E)-1-(4-carbomethoxyphenyl)-1-fluoro-2-methyl-(2,6,6-trimethyl-1-cyclohexen-1-yl)-1,3-butadiene; (E)-1-(4-carbomethoxy-2-fluorophenyl)-2-methyl-(2,6,6-trimethyl-1-cyclohexen-1-yl)-1,3-butadiene; (1Z,3E)-1-(4-carbomethoxy-2-fluorophenyl)-1-fluoro-2-methyl-(2,6,6-trimethyl-1-cyclohexen-1-yl)-1,3-butadiene; (1Z,3E)-1-(4-carbomethoxy-2-chlorophenyl)-1-fluoro-2-methyl-(2,6,6-trimethyl-1-cyclohexen-1-yl)-1,3-butadiene; (E)-1-(4-carbomethoxy-2-methylphenyl)-2-methyl-(2,6,6-trimethyl-1-cyclohexen-1-yl)-1,3-butadiene; (E)-1-(4-carbomethoxy-2-ethylphenyl)-2-methyl-(2,6,6-trimethyl-1-cyclohexen-1-yl)-1,3-butadiene; (1Z,3E)-1-(4-carbomethoxy-2-ethylphenyl)-1-fluoro-2-methyl-(2,6,6-trimethyl-1-cyclohexen-1-yl)-1,3-butadiene; (E)-1-(4-carbomethoxy-2-ethoxyphenyl)-2-methyl-(2,6,6-trimethyl-1-cyclohexen-1-yl)-1,3-butadiene; (1Z,3E)-1-(4-carbomethoxy-2-hydroxyphenyl)-1-fluoro-2-methyl-(2,6,6-trimethyl-1-cyclohexen-1-yl)-1,3-butadiene; (E)-1-(4-carbomethoxy-2-methoxyphenyl)-2-methyl-(2,6,6-trimethyl-1-cyclohexen-1-yl)-1,3-butadiene; (E)-1-(4-carboethoxy-2-fluorophenyl)-2-methyl-(2,6,6-trimethyl-1-cyclohexen-1-yl)-1,3-butadiene; (1Z,3E)-1-(4-carboethoxy-2-fluorophenyl)-1-fluoro-2-methyl-(2,6,6-trimethyl-1-cyclohexen-1-yl)-1,3-butadiene; (E)-1-(4-carboethoxy-2-chlorophenyl)-2-methyl-(2,6,6-trimethyl-1-cyclohexen-1-yl)-1,3-butadiene; (E)-1-(4-carboethoxy-2-methylphenyl)-2-methyl-(2,6,6-trimethyl-1-cyclohexen-1-yl)-1,3-butadiene; (1Z,3E)-1-(4-carboethoxy-2-ethylphenyl)-1-fluoro-2-methyl-(2,6,6-trimethyl-1-cyclohexen-1-yl)-1,3-butadiene; (E)-1-(4-carboethoxy-2-ethoxyphenyl)-2-methyl-(2,6,6-trimethyl-1-cyclohexen-1-yl)-1,3-butadiene; (E)-1-(4-carboethoxy-2-hydroxyphenyl)-2-methyl-(2,6,6-trimethyl-1-cyclohexen-1-yl)-1,3-butadiene; (1Z,3E)-1-(4-carboethoxy-2-methoxyphenyl)1-fluoro-2-methyl-(2,6,6-trimethyl-1-cyclohexen-1-yl)-1,3-butadiene; (1Z,3E)-1-(4-carboisopropoxyphenyl)-1-fluoro-2-methyl-(2,6,6-trimethyl-1-cyclohexen-1-yl)-1,3-butadiene; (E)-1-(4-carboisopropoxy-2-chlorophenyl)-2-methyl-(2,6,6-trimethyl-1-cyclohexen-1-yl)-1,3-butadiene; (1Z,3E)-1-(4-carboisopropoxy-2-methylphenyl)-1-fluoro-2-methyl-(2,6,6-trimethyl-1-cyclohexen-1-yl)-1,3-butadiene; (1Z,3E)-1-(4-carboisopropoxy-2-ethylphenyl)-1-fluoro-2-methyl-(2,6,6-trimethyl-1-cyclohexen-1-yl)-1,3-butadiene; (1Z,3E)-1-(4-carboisopropoxy-2-ethoxyphenyl)-1-fluoro-2-methyl-(2,6,6-trimethyl-1-cyclohexen-1-yl)-1,3-butadiene; (1Z,3E)-1-(4-carboisopropoxy-2-hydroxyphenyl)-1-fluoro-2-methyl-(2,6,6-trimethyl-1-cyclohexen-1-yl)-1,3-butadiene; (E)-1-(4-carboisopropoxy-2-methoxyphenyl)-2-methyl-(2,6,6-trimethyl-1-cyclohexen-1-yl)-1,3-butadiene; (1Z,3E)-1-(4-carbopropoxyphenyl)-1-fluoro-2-methyl-(2,6,6-trimethyl-1-cyclohexen-1-yl)-1,3-butadiene; (1Z,3E)-1-(4-carbopropoxy-2-chlorophenyl)-1-fluoro-2-methyl-(2,6,6-trimethyl-1-cyclohexen-1-yl)-1,3-butadiene; (E)-1-(4-carbopropoxy-2-ethylphenyl)-2-methyl-(2,6,6-trimethyl-1-cyclohexen-1-yl)-1,3-butadiene; (1Z,3E)-1-(4-carbopropoxy-2-ethoxyphenyl)-1-fluoro-2-methyl-(2,6,6-trimethyl-1-cyclohexen-1-yl)-1,3-butadiene; (E)-1-(4-carbopropoxy-2-hydroxyphenyl)-2-methyl-(2,6,6-trimethyl-1-cyclohexen-1-yl)-1,3-butadiene; (1Z,3E)-1-(4-carbopropoxy-2-methoxyphenyl)-1-fluoro-2-methyl-(2,6,6-trimethyl-1-cyclohexen-1-yl)-1,3-butadiene; (E)-1-(4-carbobutoxy-2-fluorophenyl)-2-methyl-(2,6,6-trimethyl-1-cyclohexen-1-yl)-1,3-butadiene; (E)-1-(4-carbobutoxy-2-methylphenyl)-2-methyl-(2,6,6-trimethyl-1-cyclohexen-1-yl)-1,3-butadiene; (1Z,3E)-1-(4-carbobutoxy-2-ethylphenyl)-1-fluoro-2-methyl-(2,6,6-trimethyl-1-cyclohexen-1-yl)-1,3-butadiene; (1Z,3E)-1-(4-carbobutoxy-2-hydroxyphenyl)-1-fluoro-2-methyl-(2,6,6-trimethyl-1-cyclohexen-1-yl)-1,3-butadiene; (E)-1-(4-carbobutoxy-2-methoxyphenyl)-2-methyl-(2,6,6-trimethyl-1-cyclohexen-1-yl)-1,3-butadiene; (1Z,3E)-1-(4-carbopentoxyphenyl)-1-fluoro-2-methyl-(2,6,6-trimethyl-1-cyclohexen-1-yl)-1,3-butadiene; (1Z,3E)-1-(4-carbopentoxy-2-fluorophenyl)-1-fluoro-2-methyl-(2,6,6-trimethyl-1-cyclohexen-1-yl)-1,3-butadiene; (E)-1-(4-carbopentoxy-2-methylphenyl)-2-methyl-(2,6,6-trimetmethyl-1-cyclohexen-1-yl)-1,3-butadiene; (1Z,3E)-1-(4-carbopentoxy-2-ethoxyphenyl)-1-fluoro-2-methyl-(2,6,6-trimethyl-1-cyclohexen-1-yl)-1,3-butadiene; (E)-1-(4-carbopentoxy-2-hydroxyphenyl)-2-methyl-(2,6,6-trimethyl-1-cyclohexen-1-yl)-1,3-butadiene; (1Z,3E)-1-(4-carbohexoxyphenyl)-1-fluoro-2-methyl-(2,6,6-trimethyl-1-cyclohexen-1-yl)-1,3-butadiene; (E)-1-(4-carbohexoxy-2-fluorophenyl)-2-methyl-(2,6,6-trimethyl-1-cyclohexen-1-yl)-1,3-butadiene; (1Z,3E)-1-(4-carbohexoxy-2-chlorophenyl)-1-fluoro-2-methyl-(2,6,6-trimethyl-1-cyclohexen-1-yl)-1,3-butadiene; (1Z,3E)-1-(4-carbohexoxy-2-methylphenyl)-1-fluoro-2-methyl-(2,6,6-trimethyl-1-cyclohexen-1-yl)-1,3-butadiene; (E)-1-(4-carbohexoxy-2-hydroxyphenyl)-2-methyl-(2,6,6-trimethyl-1-cyclohexen-1-yl)-1,3-butadiene; (E)-1-(4-carbohexoxy-2-methoxyphenyl)-2-methyl-(2,6,6-trimethyl-1-cyclohexen-1-yl)-1,3-butadiene; (1Z,3E)-1-(4-carboheptoxyphenyl)-1-fluoro-2-methyl-(2,6,6-trimethyl-1-cyclohexen-1-yl)-1,3-butadiene; (E)-1-(4-carboheptoxy-2-chlorophenyl)-2-methyl-(2,6,6-trimethyl-1-cyclohexen-1-yl)-1,3-butadiene; (1Z,3E)-1-(4-carboheptoxy-2-methylphenyl)-1-fluoro-2-methyl-(2,6,6-trimethyl-1-cyclohexen-1-yl)-1,3-butadiene; (1Z,3E)-1-(4-carboheptoxy-2-ethylphenyl)-1-fluoro-2-methyl-(2,6,6-trimethyl-1-cyclohexen-1-yl)-1,3-butadiene; (E)-1-(4-carboheptoxy-2-ethoxyphenyl)-2-methyl-(2,6,6-trimethyl-1-cyclohexen-1-yl)-1,3-butadiene; (1Z,3E)-1-(4-carboheptoxy-2-hydroxyphenyl)-1-fluoro-2-methyl-(2,6,6-trimethyl-1-cyclohexen-1-yl)-1,3-butadiene; (1Z,3E)-1-(4-carboctoxyphenyl)-1-fluoro-2-methyl-(2,6,6-trimethyl-1-cyclohexen-1-yl)-1,3-butadiene; (1Z,3E)-1-(4-carboctoxy-2-chlorophenyl)-1-fluoro-2-methyl-(2,6,6-trimethyl-1-cyclohexen-1-yl)-1,3-butadiene; (E)-1-(4-carboctoxy-2-methylphenyl)-2-methyl-(2,6,6-trimethyl-1-cyclohexen-1-yl)-1,3-butadiene; (E)-1-(4-carboctoxy-2-ethylphenyl)-2-methyl-(2,6,6-trimethyl-1-cyclohexen-1-yl)-1,3-butadiene; (1Z,3E)-1-(4-carboctoxy-2-ethoxyphenyl)-1-fluoro-2-methyl-(2,6,6-trimethyl-1-cyclohexen-1-yl)-1,3-butadiene; (E)-1-(4-carboctoxy-2-hydroxyphenyl)-2-methyl-(2,6,6-trimethyl-1-cyclohexen-1-yl)-1,3-butadiene; (1Z,3E)-1-(4-carbophenoxyphenyl)-1-fluoro-2-methyl-(2,6,6-trimethyl-1-cyclohexen-1-yl)-1,3-butadiene; (1Z,3E)-1-(4-carbophenoxy-2-fluorophenyl)-1-fluoro-2-methyl-(2,6,6-trimethyl-1-cyclohexen-1-yl)-1,3-butadiene; (E)-1-(4-carbophenoxy-2-chlorophenyl)-2-methyl-(2,6,6-trimethyl-1-cyclohexen-1-yl)-1,3-butadiene; (1Z,3E)-1-(4-carbophenoxy-2-ethylphenyl)-1-fluoro-2-methyl-(2,6,6-trimethyl-1-cyclohexen-1-yl)-1,3-butadiene; (E)-

1-(4-carbophenoxy-2-hydroxyphenyl)-2-methyl-(2,6,6-trimethyl-1-cyclohexen-1-yl)-1,3-butadiene; (E)-1-(4-carbophenoxy-2-methoxyphenyl)-2-methyl-(2,6,6-trimethyl-1-cyclohexen-1-yl)-1,3-butadiene; (1Z,3E)-1-(4-carbo-p-hydroxyphenoxyphenyl)-1-fluoro-2-methyl-(2,6,6-trimethyl-1-cyclohexen-1-yl)-1,3-butadiene; (E)-1-(4-carbo-p-hydroxyphenoxy-2-chlorophenyl)-2-methyl-(2,6,6-trimethyl-1-cyclohexen-1-yl)-1,3-butadiene; (E)-1-(4-carbo-p-hydroxyphenoxy-2-ethylphenyl)-2-methyl-(2,6,6-trimethyl-1-cyclohexen-1-yl)-1,3-butadiene; (E)-1-(4-carbo-p-hydroxyphenoxy-2-hydroxyphenyl)-2-methyl-(2,6,6-trimethyl-1-cyclohexen-1-yl)-1,3-butadiene; (E)-1-(4-carbo-p-hydroxyphenoxy-2-methoxyphenyl)-2-methyl-(2,6,6-trimethyl-1-cyclohexen-1-yl)-1,3-butadiene; (E)-1-(4-carbo-o-hydroxyphenoxy-2-fluorophenyl)-2-methyl-(2,6,6-trimethyl-1-cyclohexen-1-yl)-1,3-butadiene; (E)-1-(4-carbo-o-hydroxyphenoxy-2-methylphenyl)-2-methyl-(2,6,6-trimethyl-1-cyclohexen-1-yl)-1,3-butadiene; (1Z,3E)-1-(4-carbo-o-hydroxyphenoxy-2-hydroxyphenyl)-1-fluoro-2-methyl-(2,6,6-trimethyl-1-cyclohexen-1-yl)-1,3-butadiene; (1Z,3E)-1-(4-carbo-o-hydroxyphenoxy-2-methoxyphenyl)-1-fluoro-2-methyl-(2,6,6-trimethyl-1-cyclohexen-1-yl)-1,3-butadiene; (1Z,3E)-1-(4-carbo-p-methoxyphenoxyphenyl)-1-fluoro-2-methyl-(2,6,6-trimethyl-1-cyclohexen-1-yl)-1,3-butadiene; (1Z,3E)-1-(4-carbo-p-methoxyphenoxy-2-fluorophenyl)-1-fluoro-2-methyl-(2,6,6-trimethyl-1-cyclohexen-1-yl)-1,3-butadiene; (1Z,3E)-1-(4-carbo-p-methoxyphenoxy-2-ethylphenyl)-1-fluoro-2-methyl-(2,6,6-trimethyl-1-cyclohexen-1-yl)-1,3-butadiene; (E)-1-(4-carbo-p-methoxyphenoxy-2-hydroxyphenyl)-2-methyl-(2,6,6-trimethyl-1-cyclohexen-1-yl)-1,3-butadiene; (1Z,3E)-1-(4-carbo-p-isopropoxyphenoxyphenyl)-1-fluoro-2-methyl-(2,6,6-trimethyl-1-cyclohexen-1-yl)-1,3-butadiene; (1Z,3E)-1-(4-carbo-p-isopropoxyphenoxy-2-fluorophenyl)-1-fluoro-2-methyl-(2,6,6-trimethyl-1-cyclohexen-1-yl)-1,3-butadiene; (1Z,3E)-1-(4-carbo-p-isopropoxyphenoxy-2-methoxyphenyl)1-fluoro-2-methyl-(2,6,6-trimethyl-1-cyclohexen-1-yl)-1,3-butadiene; (1Z,3E)-1-(4-toloxyphenyl)-1-fluoro-2-methyl-(2,6,6-trimethyl-1-cyclohexen-1-yl)-1,3-butadiene; (E)-1-(4-toloxy-2-ethylphenyl)-2-methyl-(2,6,6-trimethyl-1-cyclohexen-1-yl)-1,3-butadiene; (1Z,3E)-1-(4-toloxy-2-hydroxyphenyl)-1-fluoro-2-methyl-(2,6,6-trimethyl-1-cyclohexen-1-yl)-1,3-butadiene; (1Z,3E)-1-(4-naphthoxy-2-fluorophenyl)-1-fluoro-2-methyl-(2,6,6-trimethyl-1-cyclohexen-1-yl)-1,3-butadiene; (E)-1-(4-naphthoxy-2-chlorophenyl)-2-methyl-(2,6,6-trimethyl-1-cyclohexen-1-yl)-1,3-butadiene; (1Z,3E)-1-(4-naphthoxy-2-ethylphenyl)-1-fluoro-2-methyl-(2,6,6-trimethyl-1-cyclohexen-1-yl)-1,3-butadiene; (1Z,3E)-1-(4-naphthoxy-2-hydroxyphenyl)-1-fluoro-2-methyl-(2,6,6-trimethyl-1-cyclohexen-1-yl)-1,3-butadiene; and (1Z,3E)-1-(4-naphthoxy-2-methoxyphenyl)1-fluoro-2-methyl-(2,6,6-trimethyl-1-cyclohexen-1-yl)-1,3-butadiene.

Examples of amides (R=NR$^1$R$^2$) represented by formula (1) are: N-methyl 4-[1-fluoro-2-methyl-4-(2,6,6-trimethyl-1-cyclohexen-1-yl)butadien-1Z,3E-yl]benzamide; N-methyl 3-fluoro-4-[1-fluoro-2-methyl-4-(2,6,6-trimethyl-1-cyclohexen-1-yl)butadien-1Z,3E-yl]benzamide; N-methyl 3-methyl-4-[1-fluoro-2-methyl-4-(2,6,6-trimethyl-1-cyclohexen-1-yl)butadien-1Z,3E-yl]benzamide; N-methyl 3-hydroxy-4-[1-fluoro-2-methyl-4-(2,6,6-trimethyl-1-cyclohexen-1-yl)butadien-1Z,3E-yl]benzamide; N-methyl 3-ethoxy-4-[1-fluoro-2-methyl-4-(2,6,6-trimethyl-1-cyclohexen-1-yl)butadien-1Z,3E-yl]benzamide; N-methyl 3-fluoro-4-[1-fluoro-2-methyl-4-(2,6,6-trimethyl-1-cyclohexen-1-yl)butadien-1Z,3E-yl]benzamide; N-methyl 3-methyl-4-[1-fluoro-2-methyl-4-(2,6,6-trimethyl-1-cyclohexen-1-yl)butadien-1Z,3E-yl]benzamide; N-methyl 3-hydroxy-4-[1-fluoro-2-methyl-4-(2,6,6-trimethyl-1-cyclohexen-1-yl)butadien-1Z,3E-yl]benzamide; N-methyl 3-methoxy-4-[1-fluoro-2-methyl-4-(2,6,6-trimethyl-1-cyclohexen-1-yl)butadien-1Z,3E-yl]benzamide; N-isopropyl 4-[1-fluoro-2-methyl-4-(2,6,6-trimethyl-1-cyclohexen-1-yl)butadien-1Z,3E-yl]benzamide; N-isopropyl 3-fluoro-4-[1-fluoro-2-methyl-4-(2,6,6-trimethyl-1-cyclohexen-1-yl)butadien-1Z,3E-yl]benzamide; N-isopropyl 3-ethyl-4-[1-fluoro-2-methyl-4-(2,6,6-trimethyl-1-cyclohexen-1-yl)butadien-1Z,3E-yl]benzamide; N-isopropyl 3-methoxy-4-[1-fluoro-2-methyl-4-(2,6,6-trimethyl-1-cyclohexen-1-yl)butadien-1Z,3E-yl]benzamide; N-isopropyl 3-chloro-4-[1-fluoro-2-methyl-4-(2,6,6-trimethyl-1-cyclohexen-1-yl)butadien-1Z,3E-yl]benzamide; N-isopropyl 3-hydroxy-4-[1-fluoro-2-methyl-4-(2,6,6-trimethyl-1-cyclohexen-1-yl)butadien-1Z,3E-yl]benzamide; N-pentyl 4-[1-fluoro-2-methyl-4-(2,6,6-trimethyl-1-cyclohexen-1-yl)butadien-1Z,3E-yl]benzamide; N-pentyl 3-fluoro-4-[1-fluoro-2-methyl-4-(2,6,6-trimethyl-1-cyclohexen-1-yl)butadien-1Z,3E-yl]benzamide; N-pentyl 3-methyl-4-[1-fluoro-2-methyl-4-(2,6,6-trimethyl-1-cyclohexen-1-yl)butadien-1Z,3E-yl]benzamide; N-pentyl 3-methoxy-4-[1-fluoro-2-methyl-4-(2,6,6-trimethyl-1-cyclohexen-1-yl)butadien-1Z,3E-yl]benzamide; N-pentyl 3-fluoro-4-[1-fluoro-2-methyl-4-(2,6,6-trimethyl-1-cyclohexen-1-yl)butadien-1Z,3E-yl]benzamide; N-pentyl 3-hydroxy-4-[1-fluoro-2-methyl-4-(2,6,6-trimethyl-1-cyclohexen-1-yl)butadien-1Z,3E-yl]benzamide; N-octyl 4-[1-fluoro-2-methyl-4-(2,6,6-trimethyl-1-cyclohexen-1-yl)butadien-1Z,3E-yl]benzamide; N-octyl 3-fluoro-4-[1-fluoro-2-methyl-4-(2,6,6-trimethyl-1-cyclohexen-1-yl)butadien-1Z,3E-yl]benzamide; N-octyl 3-ethyl-4-[1-fluoro-2-methyl-4-(2,6,6-trimethyl-1-cyclohexen-1-yl)butadien-1Z,3E-yl]benzamide; N-hydroxymethyl 4-[1-fluoro-2-methyl-4-(2,6,6-trimethyl-1-cyclohexen-1-yl)butadien-1Z,3E-yl]benzamide; N-hydroxymethyl 3-fluoro-4-[1-fluoro-2-methyl-4-(2,6,6-trimethyl-1-cyclohexen-1-yl)butadien-1Z,3E-yl]benzamide; N-hydroxymethyl 3-methyl-4-[1-fluoro-2-methyl-4-(2,6,6-trimethyl-1-cyclohexen-1-yl)butadien-1Z,3E-yl]benzamide; N-hydroxymethyl 3-hydroxy-4-[1-fluoro-2-methyl-4-(2,6,6-trimethyl-1-cyclohexen-1-yl)butadien-1Z,3E-yl]benzamide; N-hydroxymethyl 3-ethoxy-4-[1-fluoro-2-methyl-4-(2,6,6-trimethyl-1-cyclohexen-1-yl)butadien-1Z,3E-yl]benzamide; N-hydroxymethyl-3-chloro-4-[1-fluoro-2-methyl-4-(2,6,6-trimethyl-1-cyclohexen-1-yl)butadien-1,3-yl]benzamide; N-hydroxymethyl 3-hydroxy-4-[1-fluoro-2-methyl-4-(2,6,6-trimethyl-1-cyclohexen-1-yl)butadien-1Z,3E-yl]benzamide; N-(2-hydroxyethyl) 4-[1-fluoro-2-methyl-4-(2,6,6-trimethyl-1-cyclohexen-1-yl)butadien-1Z,3E-yl]benzamide; N-(2-hydroxyethyl) 3-fluoro-4-[1-fluoro-2-methyl-4-(2,6,6-trimethyl-1-cyclohexen-1-yl)butadien-1Z,3E-yl]benzamide; N-(2-hydroxyethyl) 3-chloro-4-[1-fluoro-2-methyl-4-(2,6,6-trimethyl-1-cyclohexen-1-yl)butadien-1Z,3E-yl]benzamide; N-(2-hydroxyethyl) 3-methyl-4-[1-fluoro-2-methyl-4-(2,6,6-trimethyl-1-cyclohexen-1-yl)butadien-1Z,3E-yl]benzamide; N-(2-hydroxyethyl) 3-ethyl-4-[1-fluoro-2-methyl-4-(2,6,6-trimethyl-1-cyclohexen-1-yl)butadien-1Z,3E-yl]benzamide; N-(2-hydoxyethyl) 3-hydroxy-4-[1-fluoro-2-methyl-4-(2,6,6-trimethyl-1-cyclohexen-1-yl)butadien-1Z,3E-yl]benzamide; N-(2-hydroxyethyl) 3-methoxy-4-[1-fluoro-2-methyl-4-(2,6,6-trimethyl-1- cyclohexen-1-yl)butadien-1Z,3E-yl]benzamide; N-(2-hydroxyethyl) 3-ethoxy-4-[1-fluoro-2-methyl-4-(2,6,6-trimethyl-1-cyclohexen-1-yl)butadien-1Z,3E-yl]benzamide; N-(2-hydroxyethyl) 3-fluoro-4-[1-fluoro-2-methyl-4-(2,6,6-trimethyl-1-cyclohexen-1-yl)butadien-1Z,3E-yl]benzamide; N-(2-hydroxyethyl) 3-chloro-4-[1-fluoro-2-methyl-4-(2,6,6-trimethyl-1-cyclohexen-1-yl)butadien-1Z,3E-yl]benzamide; N-(2-hydroxyethyl) 3-methyl-4-[1-fluoro-2-methyl-4-(2,6,6-trimethyl-1-cyclohexen-1-yl)butadien-1Z,3E-yl]benzamide; N-(2-hydroxyethyl) 3-ethyl-4-[1-fluoro-2-methyl-4-(2,6,6-trimethyl-1-cyclohexen-1-yl)butadien-1Z,3E-yl]benzamide; N-(2-hydroxyethyl) 3-hydroxy-4-[1-fluoro-2-methyl-4-(2,6,6-trimethyl-1-cyclohexen-1-yl)butadien-1Z,3E-yl]benzamide; N-(2-hydroxyethyl) 3-methoxy-4-[1-fluoro-2-methyl-4-(2,6,6-trimethyl-1-cyclohexen-1-yl)butadien-1Z,3E-yl]benzamide; N-(2-hydroxyethyl) 3-ethoxy-4-[1-fluoro-2-methyl-4-(2,6,6-trimethyl-1-cyclohexen-1-yl)butadien-1Z,3E-yl]benzamide; N-(3-hydroxyhexyl) 4-[1-fluoro-2-methyl-4-(2,6,6-trimethyl-1-cyclohexen-1-yl)butadien-1Z,3E-yl]benzamide; N-(3-hydroxyhexyl) 3-fluoro-4-[1-fluoro-2-methyl-4-(2,6,6-trimethyl-1-cyclohexen-1-yl)butadien-1Z,3E-yl]benzamide; N-(3-hydroxyhexyl) 3-hydroxy-4-[1-fluoro-2-methyl-4-(2,6,6-trimethyl-1-cyclohexen-1-yl)butadien-1Z,3E-yl]benzamide; N-(3-hydroxyhexyl) 3-ethoxy-4-[1-fluoro-2-methyl-4-(2,6,6-trimethyl-1-cyclohexen-1-yl)butadien-1Z,3E-yl]benzamide; N-(3-hydroxyhexyl) 3-fluoro-4-[1-fluoro-2-methyl-4-(2,6,6-trimethyl-1-cyclohexen-1-yl)butadien-1Z,3E-yl]benzamide; N-(3-hydroxyhexyl) 3-methyl-4-[1-fluoro-2-methyl-4-(2,6,6-trimethyl-1-cyclohexen-1-yl)butadien-1Z,3E-yl]benzamide; N,N-dimethyl 4-[1-fluoro-2-methyl-4-(2,6,6-trimethyl-1-cyclohexen-1-yl)butadien-1Z,3E-yl]benzamide; N,N-dimethyl 3-chloro-4-[1-fluoro-2-methyl-4-(2,6,6-trimethyl-1-cylohexen-1-yl)butadien-1Z,3E-yl]benzamide; N,N-dimethyl 3-ethyl-4-[1-fluoro-2-methyl-4-(2,6,6-trimethyl-1-cyclohexen-1-yl)butadien-1Z,3E-yl]benzamide; N,N-dimethyl 3-methoxy-4-[1-fluoro-2-methyl-4-(2,6,6-trimethyl-1-cyclohexen-1-yl)butadien-1Z,3E-yl]benzamide; N,N-dimethyl 3-fluoro-4-[1-fluoro-2-methyl-4-(2,6,6-trimethyl-1-cyclohexen-1-yl)butadien-1Z,3E-yl]benzamide; N,N-dimethyl 3-hydroxy-4-[1-fluoro-2-methyl-4-(2,6,6-trimethyl-1-cyclohexen-1-yl)butadien-1Z,3E-yl]benzamide; N-ethyl N-methyl 4-[1-fluoro-2-methyl-4-(2,6,6-trimethyl-1-cyclohexen-1-yl)butadien-1Z,3E-yl]benzamide; N-ethyl N-methyl 3-fluoro-4-[1-fluoro-2-methyl-4-(2,6,6-trimethyl-1-cyclohexen-1-yl)butadien-1Z,3E-yl]benzamide; N-ethyl N-methyl 3-hydroxy-4-[1-fluoro-2-methyl-4-(2,6,6-trimethyl-1-cyclohexen-1-yl)butadien-1Z,3E-yl]benzamide; N-ethyl N-methyl 3-methoxy-4-[1-fluoro-2-methyl-4-(2,6,6-trimethyl-1-cyclohexen-1-yl)butadien-1Z,3E-yl]benzamide; N-ethyl N-methyl 3-fluoro-4-[1-fluoro-2-methyl-4-(2,6,6-trimethyl-1-cyclohexen-1-yl)butadien-1Z,3E-yl]benzamide; N-ethyl N-methyl 3-ethyl-4-[1-fluoro-2-methyl-4-(2,6,6-trimethyl-1-cyclohexen-1-yl)butadien-1Z,3E-yl]benzamide; N-methyl N-octyl 4-[1-fluoro-2-methyl-4-(2,6,6-trimethyl-1-cyclohexen-1-yl)butadien-1Z,3E-yl]benzamide; N-methyl N-octyl 3-chloro-4-[1-fluoro-2-methyl-4-(2,6,6-trimethyl-1-cyclohexen-1-yl)butadien-1Z,3E-yl]benzamide; N-methyl N-octyl 3-ethoxy-4-[1-fluoro-2-methyl-4-(2,6,6-trimethyl-1-cyclohexen-1-yl)butadien-1Z,3E-yl]benzamide; N-methyl N-octyl 3-chloro-4-[1-fluoro-2-methyl-4-(2,6,6-trimethyl-1-cyclohexen-1-yl)butadien-1Z,3E-yl]benzamide; N-methyl N-octyl 3-hydroxy-4-[1-fluoro-2-methyl-4-(2,6,6-trimethyl-1-cyclohexen-1-yl)butadien-1Z,3E-yl]benzamide; N-phenyl 4-[1-fluoro-2-methyl-4-(2,6,6-trimethyl-1-cyclohexen-1-yl)butadien-1Z,3E-yl]benzamide; N-phenyl 3-fluoro-4-[1-fluoro-2-methyl-4-(2,6,6-trimethyl-1-cyclohexen-1-yl)butadien-1Z,3E-yl]benzamide; N-phenyl 3-hydroxy-4-[1-fluoro-2-methyl-4-(2,6,6-trimethyl-1-cyclohexen-1-yl)butadien-1Z,3E-yl]benzamide; N-phenyl 3-methoxy-4-[1-fluoro-2-methyl-4-(2,6,6-trimethyl-1-cyclohexen-1-yl)butadien-1Z,3E-yl]benzamide; N-phenyl 3-fluoro-4-[1-fluoro-2-methyl-4-(2,6,6-trimethyl-1-cyclohexen-1-yl)butadien-1Z,3E-yl]benzamide; N-phenyl 3-methyl-4-[1-fluoro-2-methyl-4-(2,6,6-trimethyl-1-cyclohexen-1-yl)butadien-1Z,3E-yl]benzamide; N-p-hydroxyphenyl 4-[1-fluoro-2-methyl-4-(2,6,6-trimethyl-1-cyclohexen-1-yl)butadien-1Z,3E-yl]benzamide; N-p-hydroxyphenyl 3-fluoro-4-[1-fluoro-2-methyl-4-(2,6,6-trimethyl-1-cyclohexen-1-yl)butadien-1Z,3E-yl]benzamide; N-p-hydroxyphenyl 3-chloro-4-[1-fluoro-2-methyl-4-(2,6,6-trimethyl-1-cyclohexen-1-yl)butadien-1Z,3E-yl]benzamide; N-p-hydroxyphenyl 3-methyl-4-[1-fluoro-2-methyl-4-(2,6,6-trimethyl-1-cyclohexen-1-yl)butadien-1Z,3E-yl]benzamide; N-p-hydroxyphenyl 3-ethyl-4-[1-fluoro-2-methyl-4-(2,6,6-trimethyl-1-cyclohexen-1-yl)butadien-1Z,3E-yl]benzamide; N-p-hydroxyphenyl 3-hydroxy-4-[1-fluoro-2-methyl-4-(2,6,6-trimethyl-1-cyclohexen-1-yl)butadien-1Z,3E-yl]benzamide; N-p-hydroxyphenyl 3-methoxy-4-[1-fluoro-2-methyl-4-(2,6,6-trimethyl-1-cyclohexen-1-yl)butadien-1Z,3E-yl]benzamide; N-p-hydroxyphenyl 3-ethoxy-4-[1-fluoro-2-methyl-4-(2,6,6-trimethyl-1-cyclohexen-1-yl)butadien-1Z,3E-yl]benzamide; N-p-hydroxyphenyl 3-fluoro-4-[1-fluoro-2-methyl-4-(2,6,6-trimethyl-1-cyclohexen-1-yl)butadien-1Z,3E-yl]benzamide; N-p-hydroxyphenyl 3-chloro-4-[1-fluoro-2-methyl-4-(2,6,6-trimethyl-1-cyclohexen-1-yl)butadien-1Z,3E-yl]benzamide; N-p-hydroxyphenyl 3-methyl-4-[1-fluoro-2-methyl-4-(2,6,6-trimethyl-1-cyclohexen-1-yl)butadien-1Z,3E-yl]benzamide; N-p-hydroxyphenyl 3-ethyl-4-[1-fluoro-2-methyl-4-(2,6,6-trimethyl-1-cyclohexen-1-yl)butadien-1Z,3E-yl]benzamide; N-p-hydroxyphenyl 3-hydroxy-4-[1-fluoro-2-methyl-4-(2,6,6-trimethyl-1-cyclohexen-1-yl)butadien-1Z,3E-yl]benzamide; N-p-hydroxyphenyl 3-methoxy-4-[1-fluoro-2-methyl-4-(2,6,6-trimethyl-1-cyclohexen-1-yl)butadien-1Z,3E-yl]benzamide; N-p-hydroxyphenyl 3-ethoxy-4-[1-fluoro-2-methyl-4-(2,6,6-trimethyl-1-cyclohexen-1-yl)butadien-1Z,3E-yl]benzamide; N-p-methoxyphenyl 4-[1-fluoro-2-methyl-4-(2,6,6-trimethyl-1-cyclohexen-1-yl)butadien-1Z,3E-yl]benzamide; N-p-methoxyphenyl 3-chloro-4-[1-fluoro-2-methyl-4-(2,6,6-trimethyl-1-cyclohexen-1-yl)butadien-1Z,3E-yl]benzamide; N-p-methoxyphenyl 3-hydroxy-4-[1-fluoro-2-methyl-4-(2,6,6-trimethyl-1-cyclohexen-1-yl)butadien-1Z,3E-yl]benzamide; N-p-methoxyphenyl 3-methoxy-4-[1-fluoro-2-methyl-4-(2,6,6-trimethyl-1-cyclohexen-1-yl)butadien-1Z,3E-yl]benzamide; N-p-methoxyphenyl 3-chloro-4-[1-fluoro-2-methyl-4-(2,6,6-trimethyl-1-cyclohexen-1-yl)butadien-1Z,3E-yl]benzamide; N-p-methoxyphenyl 3-hydroxy-4-[1-fluoro-2-methyl-4-(2,6,6-trimethyl-1-cyclohexen-1-yl)butadien-1Z,3E-yl]benzamide; N-p-methoxyphenyl 3-methoxy-4-[1-fluoro-2-methyl-4-(2,6,6-trimethyl-1-cyclohexen-1-yl)butadien-1Z,3E-yl]benzamide; N-p-butoxyphenyl 4-[1-fluoro-2-methyl-4-(2,6,6-trimethyl-1-cyclohexen-1-yl)butadien-1Z,3E-yl]benzamide; N-p-butoxyphenyl-3-fluoro-4-[1-fluoro-2-methyl-4-(2,6,6-trimethyl-1-cyclohexen-1-yl)butadien-1Z,3E-yl]benzamide; N-p-butoxyphenyl 3-ethyl-4-[1-fluoro-2-methyl-4-(2,6,6- trimethyl-1-cyclohexen-1-yl)butadien-1Z,3E-yl]benzamide; N-p-butoxyphenyl 3-fluoro-4-[1-fluoro-2-methyl-4-(2,6,6-trimethyl-1-cyclohexen-1-yl)butadien-1Z,3E-yl]benzamide; N-naphthyl 4-[1-fluoro-2-methyl-4-(2,6,6-trimethyl-1-cyclohexen-1-yl)butadien-1Z,3E-yl]benzamide; N-naphthyl 3-chloro-4-[1-fluoro-2-methyl-4-(2,6,6-trimethyl-1-cyclohexen-1-yl)butadien-1Z,3E-yl]benzamide; N-naphthyl 3-hydroxy-4-[1-fluoro-2-methyl-4-(2,6,6-trimethyl-1-cyclohexen-1-yl)butadien-1Z,3E-yl]benzamide; N-naphthyl 3-fluoro-4-[1-fluoro-2-methyl-4-(2,6,6-trimethyl-1-cyclohexen-1-yl)butadien-1Z,3E-yl]benzamide; and N-naphthyl 3-ethyl-4-[1-fluoro-2-methyl-4-(2,6,6-trimethyl-1-cyclohexen-1-yl)butadien-1Z,3E-yl]benzamide.

The retinoids of formula (1) where X is hydrogen and R is hydroxy may be made in a stereospecific manner by the following route:

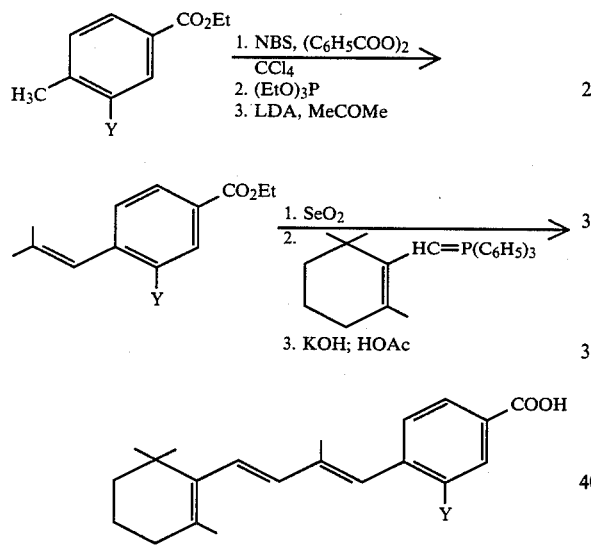

where NBS=N-bromosuccinide; Et=ethyl; LDA=lithic diisopropylamide; Me=methyl; and Ac=$H_3C$-C(O)—. Esters may be made from the acids by reaction with appropriate alcohols. The amides may be made from the acids by conversion to acid chlorides or activated esters followed by reaction with an appropriate amine.

The retinoids of formula (1) where X is fluorine and R is hydroxy may be made by the following scheme:

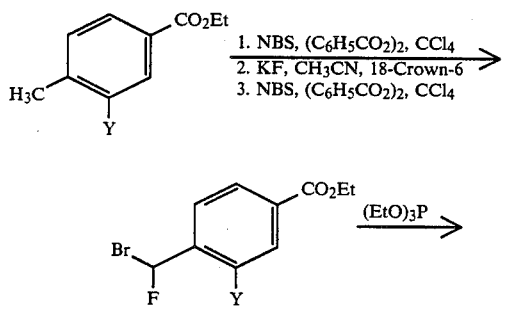

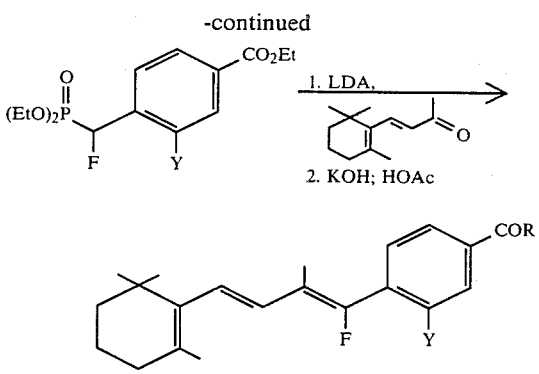

where 18-Crown-6=1,4,7,10,13,16-hexaoxacyclooctadecane and other abbreviations are as above.

The following examples further illustrate the invention compounds and their preparation. These examples are not intended to limit the invention in any manner. Abbreviations used in the examples are Me=methyl; Et=ethyl; Bu=butyl; NBS=N-bromosuccinimide; Ac=$H_3CC(O)$—; LDA=lithio diisopropylamide; THF=tetrahydrofuran; LC=high-performance liquid chromatography; IR=infrared; NMR=nuclear magnetic resonance; UV=ultraviolet; DMF=dimethylformamide; GC=gas chromatogrpahy; and TLC=thin layer chromatography.

EXAMPLE 1

Preparation of (1Z,3E)-1-(4-carbethoxyphenyl)-1-fluoro-2-methyl-4-(2,6,6-trimethyl-1-cyclohexen-1-yl)-1,3-butadiene 4-Carbethoxybenzyl Fluoride. To a solution of 7.9 g (30 mmol) of 18-crown-6 in 150 mL of $CH_3CN$ was added 35.4 g (0.60) mol of anhydrous KF (oven dried at 120° C.). The suspension was stirred at room temperature for 1 h and treated with 76.3 g (0.31 mol) of 4-carbethoxybenzyl bromide (10 mL $CH_3CN$ rinse). The reaction was heated at reflux for 92 h, cooled, and filtered. The potassium salts were washed with $CH_3CN$, and the combined filtrates were evaporated. The residue was extracted with $Et_2O$ (2×200 mL) from 300 mL of water. The extract was washed with water (2×100 mL), dried ($MgSO_4$), and concentrated to a pale yellow oil. Evaporative distillation (bath temperature 93°–110° C., 1.7 mm) yielded the product (50.0 g, 87%) as a colorless liquid: IR ($CHCl_3$) 1710 (C=O), 1610, 1580, 1460, 1410, 1365, 1275, 1230 (sh), 1170, 1105, 1010, 850 cm$^{-1}$; $^1$H NMR ($CDCl_3$) δ1.38 (t, J=7 Hz, 3, $CO_2CH_2\underline{CH_3}$), 4.36 (q, J=7 Hz, 2, $CO_2\underline{CH_2}CH_3$), 5.40 (d, J=48 Hz, 2, $CH_2F$), 7.39 (d, J=8 Hz, 2, ArH), 8.05 (d, J=8 Hz, 2, ArH o to $CO_2CH_2CH_3$); MS calcd for $C_{10}H_{11}FO_2$ 182.0743, found 182.0748.

Ethyl 4-(Bromofluoromethyl)benzoate. To a solution of 50.0 g (0.275 mol) of 4-carbethoxybenzyl fluoride in 300 mL of $CCl_4$ at reflux was added 51.0 g (0.286 mol) of NBS (recrystallized from water) containing 0.5 g (2 mmol) of benzoyl peroxide in about 1-g portions over a 1.25-h period with stirring. $CCl_4$ (50 mL total volume) was added periodically to wash in the reagent. The red suspension was heated at reflux for a further 5.5 h, cooled, and allowed to stand overnight. The succinimide was removed by filtration and rinsed with 200 mL of $CCl_4$. The combined filtrates were evaporated, and the residue was extracted with 1 L of hexane, allowed to stand for 1 h, and filtered. Concentration afforded 75.1 g of a red liquid, which was evaporatively distilled (bath temperature 85° to 95° C., 0.07–0.08 mm). The 68.7 g of pale yellow distillate was a mixture of the product and starting material by $^1$H NMR. This liquid was redistilled at 0.01 mm to give (1) a mixture of starting material and product (bp 61°–87° C.) and (2) 50.3 g (70% yield) of ethyl 4-(bromofluoromethyl)benzoate (bp 87°–95° C.) as a colorless liquid: IR (CHCl$_3$) 1715 (C=O), 1615, 1580, 1415, 1365, 1275, 1120, 1105, 1045, 860 cm$^{-1}$; $^1$H NMR (CDCl$_3$) δ1.40 (t, J=7 Hz, 3, CO$_2$CH$_2$CH$_3$), 4.38 (q, J=7 Hz, 2, CO$_2$CH$_2$CH$_3$), 7.45 (d, J=50 Hz, 1, CHF), 7.55 (d, J=8 Hz, 2, ArH), 8.10 (d, J=8 Hz, 2, ArH o to CO$_2$CH$_2$CH$_3$); MS calcd for C$_{10}$H$_{10}$BrFO$_2$ 259.9849, found 259.9872.

Diethyl 4-Carbethoxy-α-fluorobenzylphosphonate. To 9.0 g (54 mmol) of degassed (4 times, argon) triethyl phosphite at 150°–155° C. (bath temperature) was added dropwise under a stream of argon 9.4 g (36 mmol) of ethyl 4-(bromofluoromethyl)benzoate over a 20-min period. The bath temperature was raised to 200° C. and maintained there for 2.25 h. The solution, which became yellow at 200° C., was allowed to cool overnight. Triethyl phosphite was removed by distillation by heating to 130° C. (bath temperature) at 35 mm. The crude phosphonate was chromatographed on a 5×50-cm silica gel column eluted successively with 2-L portions of 50%, 75%, and 100% EtOAc/hexane to give 1.39 g of a by-product followed by 7.9 g of the phosphonate. The product was evaporatively distilled at 125°–135° C., 0.01 mm, to yield 7.72 g (68% yield) of colorless viscous liquid: IR (CHCl$_3$) 1710 (C=O), 1615, 1580, 1415, 1390, 1365, 1275, 1220 (sh), 1105, 1050 (sh), 1020, 975, 860 cm$^{-1}$; $^1$H NMR (CDCl$_3$), δ1.29 [dd, J=7 Hz, J=3 Hz, 6 P(OCH$_2$CH$_3$)$_2$], 1.40 (t, J=7 Hz, 3, CO$_2$CH$_2$CH$_3$), 4.05 [dd, J=7 Hz, J=3 Hz, 4, P(OCH$_2$CH$_3$)$_2$], 4.39 (q, J=7 Hz, 2, CO$_2$CH$_2$CH$_3$), 5.77 (dd, J=45 Hz, J=9 Hz, 1, CHFP=O), 7.55 (dd, J=8 Hz, J=1.5 Hz, 2, ArH o to CHFP=O), 8.10 (d, J=8 Hz, 2, ArH o to CO$_2$CH$_2$CH$_3$); MS calcd for C$_{14}$H$_{20}$FO$_5$P 318.1033, found 318.1045.

(1Z,3E)-1-(4-Carbethoxyphenyl)-1-fluoro-2-methyl-4-(2,6,6-trimethyl-1-cyclohexen-1-yl)-1,3-butadiene. A solution of LDA was prepared by addition of 10 mL (15 mmol) of 1.5 M n-BuLi in hexane to 2.0 g (20 mmol) of diisopropylamine in 5 mL of THF at −78° C., followed by stirring at this temperature for 20 min. Then a solution of 5.1 g (16 mmol) of diethyl 4-carbethoxy-α-fluorobenzylphosphonate in 5 mL of THF was added over a 5-min period; after 15 min a brown suspension resulted. To the reagent was added at −78° C. a solution of 4.8 g (25 mmol) of β-ionone in 5 mL of THF, and the reaction mixture was degassed (2 times, argon). After 30 min, the temperature of the reaction mixture was allowed to rise slowly from −78° C. to room temperature overnight. The resultant orange solution was poured into 250 mL of 1:1 water/saturated brine containing 2 mL of HOAc, and extracted with 9:1 hexane/Et$_2$O (2×100 mL). The extract was washed with 100 mL of 1:1 water/saturated brine and then with 100 mL of water, dried (Na$_2$SO$_4$), and concentrated to yield a viscous yellow oil. The crude product was chromatographed on a 5×45-cm silica gel column with 4% Et$_2$O/hexane to give 4.62 g (87% yield) of a mixture of the product and its 1E isomer as a yellow oil. The isomers were separated by LC in 1% Et$_2$O/hexane, using the recycle technique to yield 2.14 g (40% yield) of the 1E isomer and 2.13 g (40% yield) of the product. A 3.03-g sample of the 1Z isomer obtained from two combined reactions was finally purified by a second chromatography in 1% Et$_2$O/hexane to yield 2.69 g (36% overall yield) of pure ester: LC (Radialpak B, 1% Et$_2$O/hexane, 2.0 mL/min, 280 nm) t$_R$ 9.1 min (100%); LC (Radialpak A, 5% H$_2$O/MeOH, 2.0 mL/min, 280 nm) t$_R$ 2.5 (0.7%), 3.6 (0.4%), 4.2 (2.1%), 7.3 min (96.8%); IR (CHCl$_3$) 1710 (C=O), 1610, 1370, 1280, 1110, 1085, 1005, 970, 860 cm$^{-1}$; $^1$H NMR (CDCl$_3$) δ1.06 (s, 6, 16$_R$, 17$_R$ CH$_3$), 1.40 (t, J=7 Hz, 3, CO$_2$CH$_2$CH$_3$) 1.4–1.75 (m, 4, 2$_R$, 3$_R$ CH$_2$), 1.77 (d, J=0.5 Hz, 3, 18$_R$ CH$_3$), 1.98 (d, J=2.8 Hz, 3, 19$_R$ CH$_3$), 1.9–2.15 (m, 2, 4$_R$ CH$_2$), 4.38 (q, J=7 Hz, 2, CO$_2$CH$_2$CH$_3$), 6.27 (d, J=16 Hz, 1, 7$_R$ HC=CH), 6.76 (dd, J=16 Hz, J=2 Hz, 1, 8$_R$ HC=CH), 7.55 (d, J=8.5 Hz, 2, ArH), 8.07 (d, J=8.5 Hz, 2, ArH o to CO$_2$CH$_2$CH$_3$); $^{13}$C NMR (CDCl$_3$) 13.1 (d, J=3 Hz, 19$_R$), 14.3 (ester CH$_3$), 19.3 (3$_R$), 21.7 (18$_R$), 28.9 (16$_R$, 17$_R$), 33.0 (4$_R$), 34.2 (1$_R$), 39.6 (2$_R$), 61.0 (ester CH$_2$), 115.5 (d, J=12 Hz, 8$_R$), 127.3, 127.7, 128.1, 128.3, 128.9, 129.2, 129.8, 137.1 (d, J=28 Hz, 9$_R$), 137.7 (1'), 152.6 (d, J=247 Hz, 10$_R$), 166.0 ppm (C=O); UV (EtOH) λ$_{max}$ 322 nm (ε2.21×10$^4$), 244 nm (ε1.22×10$^4$); MS calcd for C$_{23}$H$_{29}$FO$_2$, 356.2151, found 356.2181

A sample of the 1E isomer was similarly purified in 30% overall yield: LC (Radialpak B, 1% Et$_2$O/hexane, 2.0 mL/min, 280 nm) t$_R$ 6.9 min (100%); LC (Radialpak A, 5% H$_2$O/MeOH, 2.0 mL/min, 280 nm) t$_R$ 2.2 (0.3%), 3.7 (0.7%), 4.2 (2.1%), 8.2 min (96.9%); IR (CHCl$_3$) 1710 (C=O), 1610, 1370, 1275, 1105, 1075, 1010, 860 cm$^{-1}$; $^1$H NMR (CDCl$_3$) δ1.00 (s, 6, 16$_R$, 17$_R$ CH$_3$), 1.39 (t, J=7 Hz, 3, CO$_2$CH$_2$CH$_3$), 1.35–1.7 (m, 4, 2$_R$, 3$_R$ CH$_2$), 1.68 (s, 3, 18$_R$ CH$_3$), 1.9–2.1 (m, 2, 4$_R$ CH$_2$), 2.04 (d, J=3.5 Hz, 3, 19$_R$ CH$_3$), 4.38 (q, J=7 Hz, 2, CO$_2$CH$_2$CH$_3$), 6.15 (dd, J=16 Hz, J=2 Hz, 1, 8$_R$ HC=CH), 6.35 (d, J=16 Hz, 1, 7$_R$ HC=CH), 7.52 (d, J=8 Hz, 2, ArH), 8.08 (d, J=8 Hz, 2, ArH o to CO$_2$CH$_2$CH$_3$); $^{13}$C NMR (CDCl$_3$) 11.1 (d, J=8 Hz, 19$_R$), 14.3 (ester CH$_3$), 19.2 (3$_R$), 21.7 (18$_R$), 28.9 (16$_R$, 17$_R$), 32.9 (4$_R$), 34.2 (1$_R$), 39.5 (2$_R$), 61.0 (ester CH$_2$), 116.8 (d, J=20 Hz, 8$_R$), 128.4, 128.6, 129.1, 129.3, 129.5, 130.3, 136.5 (d, J=25 Hz, 9$_R$), 137.8 (1'), 154.6 (d, J=241 Hz, 10$_R$), 165.9 ppm (C=O); UV (EtOH) λ$_{max}$ 323 nm (ε1.28×10$^4$), 252 nm (ε 1.46×10$^4$), 231 nm (ε1.59×10$^4$); MS calcd for C$_{23}$H$_{29}$FO$_2$ 356.2151, found 356.2181.

EXAMPLE 2

Preparation of (1Z,3E)-1-(4-Carboxyphenyl)-1-fluoro-2-methyl-4-(2,6,6-trimethyl-1-cyclohexen-1-yl)-1,3-butadiene To a degassed (4 times, argon) solution of 0.6 g (9.0 mmol) of 85% KOH in 1.5 mL of water and 4 mL of EtOH was added a solution of 1.26 g (3.5 mmol) of (1Z,3E)-1-(4-carbethoxyphenyl)-1-fluoro-2-methyl-4-(2,6,6-trimethyl-1-cyclohexen-1-yl)-1,3-butadiene in 3 mL of EtOH. This suspension was again degassed (2 times, argon). The reaction mixture was heated to 80° C. (bath temperature) over a 15-min period, and the temperature was maintained there for 30 min to produce a dark red solution and a precipitate. The cooled reaction mixture was quenched with 3 mL of HOAc in 5 mL of water and allowed to stand for 65 h. The yellow suspension was diluted with 30 mL of water and extracted with 50 mL of Et$_2$O. The extract was washed with water (2×25 mL) and dried (Na$_2$SO$_4$), and the solvent was evaporated. The resultant yellow powder was not very soluble in Et$_2$O, CHCl$_3$, or acetone and was therefore crystallized from 70 mL of MeOH under argon, washed with MeOH (2×3 mL), and dried to yield 896 mg (77% yield) of yellow crystals, mp 193°–194° C. The crystallization liquor was concentrated to 10 mL and cooled to yield a second crop of product (141 mg, mp 193°–194° C.). Total yield of product was 1.037 g (90%): LC (Radialpak A, 30% $H_2O$/MeOH, 2.0 mL/min, 280 nm) $t_R$ 3.2 min (100%); IR (mull) 3100–2200 (carboxyl OH), 1675 (C=O), 1595, 1450, 1420, 1370, 1315, 1285, 1180, 1075, 960, 865, 770 cm$^{-1}$; $^1$H NMR (CDCl$_3$/Me$_2$SO-d$_6$) δ1.06 (s, 6, 16$_R$, 17$_R$ CH$_3$), 1.4–1.75 (m, 4, 2$_R$, 3$_R$ CH$_2$), 1.75 (s, 3, 18$_R$ CH$_3$), 2.02 (d, J=2.8 Hz, 3, 19$_R$ CH$_3$), 1.9–2.15 (m, 2, 4$_R$ CH$_2$), 6.26 (d, J=16 Hz, 1, 7$_R$ HC=CH), 6.71 (dd, J=16 Hz, J=2 Hz, 1, 8$_R$ HC=CH), 7.55 (d, J=8.5 Hz, 2, ArH), 8.05 (d, J=8.5 Hz, 2, ArH o to CO$_2$H), 7.5–9.0 (very broad s, exchanged D$_2$O, 1, OH); $^{13}$C NMR (CDCl$_3$/Me$_2$SO-d$_6$) 10.8 (d, J=4 Hz, 19$_R$), 16.8 (3$_R$), 19.4 (18$_R$), 26.6 (16$_R$, 17$_R$), 30.6 (4$_R$), 31.8 (1$_R$), 37.2 (2$_R$), 113.0 (d, J=13 Hz, 8$_R$), 124.8, 125.2, 125.6, 125.8, 126.5, 126.7, 127.0, 127.3, 134.3 (d, J=29 Hz, 9$_R$), 135.3 (1'), 155.1 (d, 10$_R$), 165.1 ppm (C=O); UV (EtOH) λ$_{max}$ 317 nm (ε 2.02×10$^4$), 241.5 nm (ε 1.05×10$^4$); MS calcd for $C_{21}H_{25}FO_2$ 328.1828, found 328.1809.

EXAMPLE 3

Preparation of (E)-1-(4-carbethoxy-2-methoxyphenyl)-2-methyl-4-(2,6,6-trimethyl-1-cyclohexen-1-yl)-1,3-butadiene Methyl 3-Methoxy-4-methylbenzoate. A mixture of 30 g (0.20 mol) of 3-hydroxy-4-methylbenzoic acid, 68.1 g (0.49 mol) of K$_2$CO$_3$, and 123 mL (1.98 mol) of MeI in 250 mL of DMF was heated at reflux for 19 h. After cooling to room temperature, the reaction mixture was diluted with 500 mL of water and extracted with Et$_2$O (2×300 mL). The organic phase was washed with water and brine, dried (MgSO$_4$), and concentrated to 37 g of orange oil: TLC (5% Et$_2$O/hexane) R$_f$ 0.13 (3-hydroxy-4-methylbenzoic acid), 0.63 (methyl 3-methoxy-4-methylbenzoate), and 0.72. The oil was chromatographed on 450 g of silica gel with 5% Et$_2$O/hexane (100-mL fractions) to give 19.5 g of methyl 3-methoxy-4-methylbenzoate and 6.6 g of methyl 3-methoxy-4-methylbenzoate contaminated with the higher R$_f$ material. The impure fraction was chromatographed on 250 g of silica gel to afford an additional 5.6 g of product. The total yield of white crystalline solid, mp 50°–51° C., was 25.1 g (72%). A sample from an earlier experiment was characterized: IR (film) 1700, 1400, 1290, 1270, 1100 cm$^{-1}$; $^1$H NMR (CDCl$_3$) δ 2.25 (s, 3, ArCH$_3$), 3.85 and 3.88 (2 s, 6, CO$_2$CH$_3$ ArOCH$_3$), 7.2–7.9 (m, 3, ArH); MS calcd for $C_{10}H_{12}O_3$ 180.0786, found 180.0779.

Ethyl 4-Bromomethyl-3-methoxybenzoate. A 19.0-g (0.11-mol) portion of methyl 3-methoxy-4-methylbenzoate was dissolved in 100 mL of EtOH, and 2 mL of concentrated H$_2$SO$_4$ was added. This solution was heated at reflux for 4 days, at which time GC analysis (0.125-in×6-ft 3% OV-1 column, 100° to 250° C., 16° C./min) of an aliquot, which had been diluted with Et$_2$O and washed with water, indicated two peaks at 3.25 and 3.75 min, corresponding to methyl 3-methoxy-4-methylbenzoate and ethyl 3-methoxy-4-methylbenzoate, respectively. Another 2-mL portion of acid was added and heating was continued for 4 more days, when GC analysis indicated the disappearance of starting material. The cooled reaction mixture was diluted with Et$_2$O and washed with water and brine, dried (Na$_2$SO$_4$), and concentrated to afford 19.7 g (97% crude yield) of the ethyl ester as a white solid: IR (CHCl$_3$) 1710, 1470, 1410, 1290, 1270, 1110, 1040 cm$^{-1}$; $^1$H NMR (CDCl$_3$) δ 1.38 (t, J=7 Hz, 3, CO$_2$CH$_2$CH$_3$), 2.23 (s, 3, ArCH$_3$), 3.87 (s, 3, OCH$_3$), 4.40 (q, J=7 Hz, 2, CO$_2$CH$_2$CH$_3$), 7.1–7.8 (m, 3, ArH).

A mixture of 17.9 g (0.09 mol) of crude ethyl 3-methoxy-4-methylbenzoate, 19.69 g (0.11 mol) of NBS (recrystallized from water), and 4 grains of benzoyl peroxide in 250 mL of CCl$_4$ was heated at reflux for 1 h, at which time TLC (7% Et$_2$O/hexane) indicated two spots with R$_f$ values of 0.41 (ethyl 4-bromomethyl-3-methylbenzoate) and 0.52 (ethyl 3-methoxy-4-methylbenzoate). More benzoyl peroxide (4 grains) was added to the reaction mixture and heating was continued for 2 h more, when TLC indicated only a trace of ethyl 4-bromomethyl-3-methylbenzoate. The reaction mixture was cooled to room temperature and filtered (CCl$_4$ rinse). Concentration of the filtrate afforded 27.9 g of an oil, which was chromatographed on 800 g of silica gel with 10% Et$_2$O/hexane (500-mL fractions). Fractions 9 to 15 contained 27.0 g (98% yield) of product as a white solid, mp 57°–63° C.: IR (CHCl$_3$) 1710, 1410, 1290, 1100 cm$^{-1}$; $^1$H NMR δ 1.37 (t, J=6 Hz, 3, CO$_2$CH$_2$CH$_3$), 3.97 (s, 3, OCH$_3$), 4.40 (q, J=6 Hz, 2, CO$_2$CH$_2$CH$_3$) 4.85 (s, 2, CH$_2$Br), 7.3–8.1 (m, 3, ArH); MS calcd for $C_{11}H_{12}O_3Br$ 270.9970, found 270.9962.

Diethyl 4-Carbethoxy-2-methoxybenzylphosphonate. A mixture of 48.2 g (0.175 mol) of ethyl 4-bromomethyl-3-methylbenzoate and 46.0 mL (0.27 mol) of (EtO)$_3$P was heated under a stream of argon in a 50°–55° C. oil bath for 20 min. The bath temperature was then raised to 200° C. for 2 h while the EtBr was allowed to distill off. The bath temperature was next raised to 250° C. to remove unreacted (EtO)$_3$P at 14 mm. The dark brown residue was chromatographed on 450 g of silica gel with 15.5 L of 50% EtOAc/hexane, 7 L of 75% EtOAc/hexane, and 100% EtOAc. Fractions 9 to 38 (500 mL) contained, after concentration, 36.0 g of crude product, which was rechromatographed on 1400 g of silica gel with 21 L of 75% EtOAc/hexane, followed by EtOAc. Fractions 15 to 44 contained, after concentration, 32.3 g of a viscous yellow oil: TLC (50% EtOAc/hexane) R$_f$ 0.25. Evaporative distillation at 144°–150° C. (200–250 mm) afforded 30.6 g (53% yield) of product as a colorless viscous oil: IR (film) 1720, 1415, 1280, 1230, 1100, 1040, 960 cm$^{-1}$, $^1$H NMR (CDCl$_3$) δ 1.24 (t, J=7 Hz, 6, P(OCH$_2$CH$_3$)$_2$), 1.35 (t, J=7 Hz, 3, CO$_2$CH$_2$CH$_3$), 3.26 (d, J=22 Hz, 2, PCH$_2$Ar), 3.90 (s, 3, OCH$_3$), 4.12 (q, J=7 Hz, 4, P(OCH$_2$CH$_3$)$_2$), 4.40 (q, J=7 Hz, 2, CO$_2$CH$_2$CH$_3$), 7.33 (d, J=8 Hz, 1, 6' H), 7.58 (broad s, 1, 3' H), 7.62 (d, J=8 Hz, 1, 5' H): MS calcd for $C_{15}H_{23}O_6P$ 330.1234, found 330.1212.

Ethyl 4-(2,2-Dimethylvinyl)-3-methoxybenzoate. A 3.42-g (84.2-mmol) portion of 59% NaH-mineral dispersion was washed with pentane (20 mL, 2×10 mL). To the NaH remaining was added with stirring 85 mL of DMF followed by 27.8 g (84.2 mmol) of diethyl 4-carbethoxy-2-methoxybenzylphosphonate in 10 mL of DMF (5-mL DMF rinse). The reaction mixture turned deep yellow. After 3.5 h of stirring, when hydrogen evolution ceased, 32.0 mL (436 mmol) of acetone was added with cooling in a cold water bath to maintain the internal temperature at 20°–30° C. The orange reaction mixture was then stirred at room temperature for 13 h before dilution with 600 mL of Et$_2$O and 400 mL of H$_2$O containing 4 mL of HOAc. The aqueous layer was extracted with 400 mL of Et$_2$O. The combined Et$_2$O extracts were washed with water (3×100 mL) and brine (2×100 mL), dried (MgSO$_4$), and concentrated to 19.8 g of a yellow oil. This material was chromatographed on 500 g of silica gel with 10% Et$_2$O/hexane to afford in fractions 15 to 23 (125-mL volume) 14.4 g (73% yield) of a colorless oil (TLC R$_f$ 0.27), which solidified to off-white prisms, mp 42° C.; IR (film) 1720, 1470, 1420, 1300, 1280, 1260, 1110, 1040 cm$^{-1}$; $^1$H NMR (CDCl$_3$) δ 1.40 (t, J=7 Hz, 3, CO$_2$CH$_2$CH$_3$), 1.82 (d, J=0.5 Hz, 3, C=CCH$_3$), 1.98 (d, J=0.5 Hz, 3, C=CCH$_3$), 3.90 (s, 3, OCH$_3$), 4.42 (q, J=7 Hz, 2, CO$_2$CH$_2$CH$_3$), 6.38 (broad s, 1, C=CH), 7.26 (d, J=8 Hz, 1, 5' H), 7.60 (d, J=2 Hz, 1, 2' H), 7.70 (dd, J=8 Hz, J=2 Hz, 1, 6' H); MS calcd for C$_{14}$H$_{18}$O$_3$ 234.1256, found 234.1259. Further elution of the column afforded a viscous yellow oil (R$_f$ 0.19).

(E)-3-(4-Carbethoxy-2-methoxyphenyl)-2-methylpropenal. A mixture of 1.0 g (4.3 mmol) of ethyl 4-(2,2-dimethylvinyl)-3-methoxybenzoate, 1.24 g (11.2 mmol) of SeO$_2$, and 0.2 mL of water in 15 mL of dioxane was heated in a 110° C. oil bath for 1.5 h. After cooling to room temperature, the reaction mixture was filtered through Celite (Et$_2$O rinse) to remove excess SeO$_2$. Concentration afforded an orange semisolid residue, which was dissolved in a small amount of toluene and chromatographed on 25 g of silica gel using 30% Et$_2$O/hexane to afford a small amount of a yellow oil (R$_f$ 0.64, Z-isomer) followed by 0.60 g of a yellow solid (R$_f$ 0.56, E-isomer). This solid was rechromatographed on 20 g of silica gel (toluene) to remove colored by-products (R$_f$ 0.0, 0.38) and to isolate the aldehyde (R$_f$ 0.18), which was submitted to evaporative distillation at 110°-120° C. (0.005 mm) to afford 0.45 g (42% yield) of very pale yellow solid. The $^1$H NMR spectrum indicated none of the Z-isomer was present. A sample was purified by crystallization from EtOAc/hexane: white prisms, mp 59°-61° C.; IR (CHCl$_3$) 2840, 1705, 1675, 1410, 1290, 1110, 1010 cm$^{-1}$; $^1$H NMR (CDCl$_3$) δ 1.42 (t, J=7 Hz, 3, CO$_2$CH$_2$CH$_3$), 2.0 (d, J=0.5 Hz, 3, C=CCH$_3$), 3.95 (s, 3, OCH$_3$), 4.42 (q, J=7 Hz, 2 CO$_2$CH$_2$CH$_3$), 7.3-7.85 (m, 4, C=CH, 3', 5', 6' H), 9.67 (s, 1, CHO); MS calcd for C$_{14}$H$_{16}$O$_4$ 248.1049, found 248.1058.

(E)-1-(4-Carbethoxy-2-methoxyphenyl)-2-methyl-4-(2,6,6,-trimethyl-1-cyclohexen-1-yl)-1,3-butadiene. To a suspension of 10.59 g (22.1 mmol) of β-cyclogeranyltriphenylphosphonium bromide in 225 mL of THF, which was stirred in a dry ice/CCl$_4$ bath, 12.7 mL (19.6 mmol) of 1.54 M n-BuLi in hexane was added over a period of 15 min. This deep red reaction mixture was next stirred in an ice bath for 10 min before a solution of 4.98 g (20.1 mmol) of (E)-3-(4-carbethoxy-2-methoxyphenyl)-2-methylpropenal in 25 mL of THF (5 mL THF rinse) was added. The reaction mixture was degassed three times under argon and stirred at room temperature for 19 h, at which time the color had faded to light orange. The reaction mixture was diluted with 500 mL of hexane, 250 mL of Et$_2$O, and 500 mL of H$_2$O. The aqueous phase was extracted with 500 mL of hexane. The organic extracts were washed with two 250-mL portions of water and brine, dried (MgSO$_4$), and concentrated to a yellow semisolid, which on extraction with 10% Et$_2$O/hexane and concentration gave 8.3 g of a yellow oil, which was chromatographed on 400 g of silica gel with 10% Et$_2$O/hexane (200-mL fractions). Fractions 8 to 11 afforded 6.8 g of a pale yellow oil. Further elution with 30% Et$_2$O/hexane afforded 1.3 g of recovered aldehyde. The crude diene mixture was purified by preparative LC using the recycle technique (2% ether/hexane) to afford 2.9 g (40% yield) of pale yellow, viscous oil, which solidified to off-white prisms, mp 74°-76° C., on standing: LC (Radialpak B, 2.5% Et$_2$O/hexane, 2 mL/min, 260 nm) t$_R$ 10.0 (0.5%), 11.1 (99.2%), 12.1 min (0.3%); LC (Radialpak A, 20% water/MeCN, 2 mL/min, 260 nm) t$_R$ 3.0 (2.7%), 34.0 min (97.3%); IR (CHCl$_3$) 1705 (C=O), 1290, 1270, 1110 cm$^{-1}$; 300 MHz $^1$H NMR δ 1.05 (s, 6, 16$_R$, 17$_R$ CH$_3$), 1.40 (t, J=7 Hz, 3, CO$_2$CH$_2$CH$_3$), 1.48 and 1.63 (2 m, 4, 2$_R$, 3$_R$ CH$_2$), 1.75 (s, 3, 18$_R$ CH$_3$), 2.03 (s, 3, 19$_R$ CH$_3$), 2.03 (m, 2, 4$_R$ CH$_2$), 3.90 (s, 3, OCH$_3$), 4.39 (q, J=7 Hz, 2, CO$_2$CH$_2$CH$_3$), 6.13 (d, J=16 Hz, 1, 7$_R$ HC=CH), 6.40 (d, J=16 Hz, 1, 8$_R$ HC=CH), 6.57 (s, 1, 10$_R$ C=CH), 7.33 (d, J=9 Hz, 1, 6' H), 7.53 (d, J=1.3 Hz, 1, 3' H), 7.65 (dd, J=1.7 Hz, J=9 Hz, 1, 5' H); $^{13}$C NMR (CDCl$_3$) δ 14.2*, 14.4* (19$_R$, OCH$_2$CH$_3$), 19.3 (3$_R$), 21.8 (18$_R$), 29.0 (16$_R$, 17$_R$), 33.1 (4$_R$), 34.3 (1$_R$), 39.7 (2$_R$), 55.6 (OCH$_3$), 60.9 (OCH$_2$), 111.0 (3'), 121.5 (1'), 124.4 (5'), 127.6 (6'), 129.7 (7$_R$), 130.1 (5$_R$), 131.9 (4'), 137.7 (6$_R$), 138.0 (8$_R$, 9$_R$, 10$_R$), 157.1 (2'), 166.5 ppm (C=O); UV (EtOH) λ$_{max}$ 230 nm (shoulder, ε 1.34×10$^4$); 330 nm (ε 2.76×10$^4$); MS calcd for C$_{24}$H$_{32}$O$_3$ 368.2351, found 368.2377.

*Assignments of adjacent signals may be interchanged.

EXAMPLE 4

Preparation of (E)-1-(4-Carboxy-2-methoxyphenyl)-2-methyl-4-(2,6,6-trimethyl-1-cyclohexen-1-yl)-1,3-butadiene A solution of 1.2 g (21.4 mmol) of KOH in 3 mL of H$_2$O and 5 mL of EtOH was degassed four times under argon and added to a suspension of 2.0 g (5.42 mmol) of the ethyl ester of Example 3 in 5 mL of EtOH. The mixture was degassed four times and heated at 80° C. for 30 min. The cooled solution was acidified with 12 mL of 50% HOAc and diluted with 30 mL of H$_2$O and 35 mL of Et$_2$O. The aqueous layer was extracted again with 35 mL of Et$_2$O. The combined Et$_2$O layers were washed with brine (2×50 mL) and dried (Na$_2$SO$_4$). Concentration gave 1.84 g (100% yield) of pale yellow solid. Recrystallization from cold EtOAc and hexane yielded 764 mg (41% yield) of pale yellow powder, mp 156°-157° C. The mother liquor was concentrated and recrystallized from cold EtOAc, yielding 450 mg (24% yield) of fine yellow crystals, mp 157°-158° C. The overall yield was 65%. LC (μ Bondapak C$_{18}$, 50% H$_2$O/MeCN, 2 mL/min, 260 nm) t$_R$ 7.6 min (99.7%, both crops); IR (CHCl$_3$) 3520, 2930 (broad), 2600 (broad), 1685, 1600, 1575, 1500, 1460, 1420, 1360, 1300-1200 (broad), 1180, 1120, 1040, 975, 920, 880 cm$^{-1}$; 300 MHz $^1$H NMR (CDCl$_3$) δ 1.05 (s, 6, 16$_R$, 17$_R$ CH$_3$), 1.46-1.65 (m, 4, 2$_R$,3$_R$ CH$_2$), 1.76 (s, 3, 18$_R$ CH$_3$), 2.04 (s, 3, 19$_R$ CH$_3$), 2.04 (m, 2, 4$_R$ CH$_2$), 3.92 (s, 3, OCH$_3$), 6.15 (d, J=16 Hz, 1, 7$_R$ HC=CH), 6.42 (d, J=16 Hz, 1, 8$_R$ HC=CH), 6.58 (s, 1, 10$_R$ C=CH), 7.38 (d, J=8 Hz, 1, 6' H), 7.59 (d, J=1 Hz, 1, 3' H), 7.74 (d, J=1 Hz, J=8 Hz, 1, 5' H), 12.15 (very broad s, 0.5, CO$_2$H); $^{13}$C NMR (CDCl$_3$) 14.3 (19$_R$), 19.3 (3$_R$), 21.8 (18$_R$), 29.0 (16$_R$, 17$_R$), 33.1 (4$_R$), 34.3 (1$_R$), 39.7 (2$_R$), 55.6 (OCH$_3$), 111.4 (3'), 122.8 (1'), 124.2 (5'), 127.9 (6'), 128.3 (4'), 129.4 (7$_R$), 130.2 (5$_R$), 133.1 (10$_R$), 137.6 (6$_R$), 138.0 and 138.4 (8$_R$,9$_R$), 151.7 (2'), 172.4 ppm (C=O); UV (MeCN) λ$_{max}$ 328 nm (ε 2.5×10$^4$); MS calcd for C$_{22}$H$_{28}$O$_3$ 340.2038, found 340.2036.

EXAMPLE 5

Preparation of
(E)-1-(4-Carbethoxy-2-fluorophenyl)-2-methyl-4-(2,6,6-trimethyl-1-cyclohexen-1-yl)-1,3-butadiene Ethyl 4-Bromomethyl-3-fluorobenzoate. A solution of 10.2 g (66.2 mmol) of 3-fluoro-4-methylbenzoic acid in 50 mL of EtOH and 25 mL of toluene containing 0.2 mL of $H_2SO_4$ was heated gradually to 120° C. (oil bath temperature), and the solvent was removed by distillation over a period of 2.25 h through a 10-cm Vigreux column. The residue was cooled, treated with a further 50 mL of EtOH and 25 mL of toluene, and the distillation was repeated. The residual solution, containing some white solid, was poured into 75 mL of aqueous $NaHCO_3$ and extracted with hexane (75 mL, then 50 mL). The extract was washed with water (2×75 mL), dried ($Na_2SO_4$), and concentrated. The pale-yellow liquid was distilled, bp 49°–58° C. (0.01–0.05 mm) to give 11.1 g (92% yield) of ethyl 3-fluoro-4-methylbenzoate as a colorless liquid: IR ($CHCl_3$) 1720 (C=O), 1580, 1420, 1370, 1290, 1190, 1130, 1090, 1020, 940, 895 cm$^{-1}$; $^1$H NMR ($CDCl_3$) δ 1.40 (t, J=7 Hz, 3, $CO_2CH_2CH_3$), 2.32 (d, J=2 Hz, 3, $ArCH_3$), 4.37 (q, J=7 Hz, 2, $CO_2CH_2CH_3$), 7.22 (dd, J=8 Hz, J=8 Hz, 1, 6' H), 7.68 (m, 2, 3', 5' H); MS calcd for $C_{10}H_{11}FO_2$ 182.0743, found 182.0729.

To a solution of 10.95 g (60.1 mmol) of ethyl 3-fluoro-4-methylbenzoate in 60 mL of $CCl_4$ was added over 30 min a mixture of 12.8 g (72 mmol) of recrystallized (water) NBS and 125 mg (0.52 mmol) of benzoyl peroxide (5 mL $CCl_4$ rinse). The suspension was heated at reflux with stirring for 14 h, cooled, and filtered. The precipitate of succinimide was washed with 200 mL of hexane. The combined filtrates were filtered again, and the filtrate was concentrated to give a light-orange liquid. Distillation through a 10-cm Vigreux column yielded successively 0.50 g (4.5% recovery) of unreacted ethyl ester, bp 55°–60° C. (0.01 mm), 8.13 g (52% yield) of the product as a colorless liquid, bp 94°–104° C. (0.01 mm), and 5.75 g of a mixture of the product and ethyl 4-dibromomethylbenzoate, bp 104°–115° C. (0.01 mm). The latter fraction was redistilled to give 3.41 g (21% yield) of additional ethyl 4-bromomethyl-3-fluorobenzoate, bp 101°–108° C. (0.05 mm). The total yield was 11.54 g (73%) of white crystals, mp 42.5°–44° C. (pentane): IR ($CHCl_3$) 1720 (C=O), 1585, 1425, 1375, 1290, 1105, 1090, 1020, 950, 900 cm$^{-1}$; $^1$H NMR ($CDCl_3$) δ 1.40 (t, J=7 Hz, 3, $CO_2CH_2CH_3$), 4.40 (q, J=7 Hz, 2, $CO_2CH_2CH_3$), 4.52 (s, 2, $CH_2Br$), 7.60 (m, 3, 3', 5', 6' H); MS calcd for $C_{10}H_{10}BrFO_2$ 259.9849, found 259.9860.

Diethyl 4-Carbethoxy-2-fluorobenzylphosphonate. To 9.0 g (54.2 mmol) of degassed (argon) $(EtO)_3P$ heated under a stream of argon in a 150° C. oil bath was added over a 25-min period 9.4 g (36.0 mmol) of ethyl 4-bromomethyl-3-fluorobenzoate. A pale-yellow solution resulted. The heating bath temperature was raised to 200°–205° C. over a period of 25 min and the temperature maintained there for 55 min. The bright yellow liquid was then cooled and chromatographed on a silica gel column (4×40 cm) with 1.5-L portions of 25% and 75% EtOAc/hexane and EtOAc to give 9.8 g of the crude phosphonate as a yellow viscous oil. Evaporative distillation at 130°–140° C. (0.05–0.1 mm) produced 9.34 g (82% yield) of product as a colorless, viscous oil: IR ($CHCl_3$) 1710 (C=O), 1580, 1420, 1390, 1365, 1280 (1240 sh), 1090, 1020 (1040 sh), 960, 895, 850 cm$^{-1}$; $^1$H NMR ($CDCl_3$) δ 1.28 (t, J=7 Hz, 6, $OP(OCH_2CH_3)_2$), 1.40 (t, J=7 Hz, 3, $CO_2CH_2CH_3$), 3.30 (d, J=22 Hz, 2, $CH_2PO$), 4.03 (q, J=7 Hz, 4, $P(OCH_2CH_3)_2$), 4.40 (q, J=7 Hz, 2, $CO_2CH_2CH_3$), 7.65 (m, 3, 3', 5', 6' H); MS calcd for $C_{14}H_{20}FO_5$ 318.1033, found 318.1058.

1-(4-Carbethoxy-2-fluorophenyl)-2-methylpropene. To 2 mL (14 mmol) of diisopropylamine in 5 mL of $Et_2O$, which was kept at ice-bath temperature under argon, was added 8.0 mL (11.1 mmol) of a 1.39 M solution of n-BuLi in hexane. This solution of LDA was stirred for 45 min, cooled in a −20° C. bath, and treated with a solution of 3.61 g (11.3 mmol) of diethyl 4-carbethoxy-2-fluorobenzylphosphonate in 6 mL of THF. The reaction mixture was stirred for 30 min to give a red gum and solution. Next, a solution of 0.85 mL (11.7 mmol) of acetone in 3 mL of THF was added, the cooling bath was removed, and the reaction mixture was shaken to give a red-brown solution. The reaction mixture was then stirred at room temperature for 65 min, quenched with 20 mL of water containing 1 mL (18.3 mmol) of HOAc, diluted with 50 mL of brine, and extracted with $Et_2O$ (2×25 mL). The extract was washed with water (2×20 mL), dried (MgSO$_4$), and concentrated. Chromatography on a 3×35 cm silica gel column with 500 mL of 3%, 300 mL of 10%, and 800 mL of 75% EtOAc/hexane gave 1.405 g (57% yield) of product as a colorless liquid: IR ($CHCl_3$) 1720 (C=O), 1665 (C=C), 1625, 1575, 1505, 1450, 1420, 1375, 1290, 1195, 1115, 1090, 1020, 945, 895, 860 cm$^{-1}$; $^1$H NMR ($CDCl_3$) δ 1.39 (t, J=7 Hz, 3, $CO_2CH_2CH_3$), 1.83 and 1.97 (2 s, 6, C=C($CH_3$)$_2$), 4.40 (q, J=7 Hz, 2, $CO_2CH_2CH_3$), 6.29 (s, 1, C=CH), 7.33 (dd, J=8 Hz, J=8 Hz, 1, 6' H), 7.77 (m, 2, 3', 5' H); UV (EtOH) $\lambda_{max}$ 270 nm (ε 1.61×10$^4$); MS calcd for $C_{13}H_{15}FO_2$ 222.1056, found 222.1062.

(E)-3-(4-Carbethoxy-2-fluorophenyl)-2-methylpropenal. A suspension of 1.28 g (11.55 mmol) of SeO$_2$ in 65 mL of dioxane containing 1.72 g (7.7 mmol) of 1-(4-carbethoxy-2-fluorophenyl)-2-methylpropene was degassed three times under argon, heated at reflux for 3.25 h, and cooled. The precipitate of Se was removed by filtration and washed with 20 mL of dioxane. The filtrate and wash were concentrated. The residue was chromatographed on a 3×30 cm silica gel column with 800-mL volumes of 8% and 10% EtOAc/hexane. Fractions containing mixtures of the E and Z-aldehydes were rechromatographed on a 2×25 cm silica gel column with 8% EtOAc/hexane to yield (a) 16 mg (1% yield) of the Z-aldehyde: IR ($CHCl_3$) 1710 (C=O), 1680 (C=O), 1610, 1570, 1410, 1370, 1345, 1280 (1240 sh), 1180, 1110 (1120 sh), 1015, 890, 855 cm$^{-1}$; $^1$H NMR ($CDCl_3$) δ 1.45 (t, J=7 Hz, 3, $CO_2CH_2CH_3$), 2.02 (d, J=1.5 Hz, 3, C=CCH$_3$), 4.40 (q, J=7 Hz, 2, $CO_2CH_2CH_3$), 7.57 (m, 3, 3', 5', 6' H), 9.85 (d, J=2 Hz, 1, CHO); (b) 44 mg (2% yield of a mixture of the E and Z-aldehydes; and (c) 1.16 g (63% yield) of the E-aldehyde as white crystals, mp 46.5°–47° C. (EtOAc/hexane): IR ($CHCl_3$) 1680 (C=O) (1710 sh, C=O), 1630, 1610, 1570, 1400, 1370, 1285 (1240 sh), 1180, 1105, 1010, 890, 860 cm$^{-1}$; $^1$H NMR ($CDCl_3$) δ 1.43 (t, J=7 Hz, 3, $CO_2CH_2CH_3$), 2.05 (s, 3, C=CCH$_3$), 4.43 (q, J=7 Hz, 2, $CO_2CH_2CH_3$), 7.48 (m, 1, 6' H), 7.70 (dd, J=7 Hz, J=1 Hz, 1, 3' H), 7.90 (s, 1, C=CH), 7.97 (dd, J=7 Hz, J=2 Hz, 1, 5' H), 9.72 (s, 1, CHO); UV (MeCN) $\lambda_{max}$ 278 nm (ε 1.94×10$^4$); MS calcd for $C_{13}H_{13}FO_3$ 236.0849, found 236.0835.

(E)-1-(4-Carbethoxy-2-fluorophenyl)-2-methyl-4-(2,6,6-trimethyl-1-cyclohexen-1-yl)-1,3-butadiene. To a suspension of 3.6 g (7.5 mmol) of β-cyclogeranyltriphenylphosphonium bromide in 15 mL of THF at −25° C. was added 5.0 mL (6.95 mmol) of a 1.39 M solution of n-BuLi in hexane. The reaction was allowed to warm to 0° C. over a 45-min period. Then 1.11 g (4.7 mmol) of (E)-3-(4-carbethoxy-2-fluorophenyl)-2-methylpropenal in 6 mL of THF was added. The mixture was allowed to warm to room temperature over 1.5 h before the dark-orange suspension was quenched with 10 mL of 10% aqueous HOAc and diluted with 50 mL of water. The product was extracted into 30 mL of 10% EtOAc/hexane, washed with water (2×30 mL), dried ($Na_2SO_4$), and concentrated. The crude product was eluted through a 3×30 cm silica gel column with 3% EtOAc/hexane to give 1.68 g of pale yellow liquid, which was purified twice by preparative LC (2% $Et_2O$/hexane) using the recycle technique to give 1.13 g (67% yield) of product ester as a pale-yellow gum: LC (Radialpak B, 1% $Et_2O$/hexane, 2.0 mL/min, 280 nm) $t_R$ 4.1 min (100%); LC (Radialpak A, 5% $H_2O$/MeCN, 2.0 mL/min, 280 nm) $t_R$ 11.9 (sh, 1.2%), 12.5 (97.6%), 13.3 min (sh, 1.2%); IR ($CHCl_3$) 1705 (C=O), 1605, 1555, 1435, 1410, 1360, 1285, 1180, 1110, 1080, 1010, 960, 935, 885, 855 cm$^{-1}$; 360 MHz $^1$H NMR ($CDCl_3$) δ 1.05 (s, 6, $16_R, 17_R$ $CH_3$), 1.40 (t, J=7 Hz, 3, $CO_2CH_2CH_3$), 1.48 and 1.63 (2 m, 4, $2_R, 3_R$ $CH_2$), 1.75 (s, 3, $18_R$ $CH_3$), 2.02 (s, 3, $19_R$ $CH_3$), 2.03 (m, 2, $4_R$ $CH_2$), 4.38 (q, J=7 Hz, 2, $CO_2CH_2CH_3$), 6.24 (d, J=16 Hz, 1, $8_R$ HC=CH), 6.32 (d, J=16 Hz, 1, $7_R$ HC=CH), 6.46 (s, 1, $10_R$ C=CH), 7.40 (dd, J=8 Hz, J=8 Hz, 6' H), 7.71 (dd, J=10.5 Hz, J=1.5 Hz, 1, 3' H), 7.80 (dd, J=8 Hz, J=1.5 Hz, 1, 5' H); $^{13}$C NMR ($CDCl_3$) 14.2 and 14.3 ($19_R$, $CH_2CH_3$), 19.2 ($3_R$), 21.7 ($18_R$), 28.9 ($16_R, 17_R$), 33.0 ($4_R$), 34.2 ($1_R$), 39.5 ($2_R$), 61.2 ($OCH_2$), 116.3 (d, J=25 Hz, 3'), 121.1 (5'), 124.7 (6'), 128.8 ($10_R$), 129.7 ($5_R$), 130.1 (4'), 130.5 ($7_R$, 1'), 137.4 ($6_R, 8_R$), 140.0 ($9_R$), 159.8 (d, J=148 Hz, 2'), 165.5 ppm (C=O); UV (EtOH) $\lambda_{max}$ 318 nm (ε 2.31×10$^4$); MS calcd for $C_{23}H_{29}FO_2$ 356.2151, found 356.2163.

EXAMPLE 6

Preparation of
(E)-1-(4-Carboxy-2-fluorophenyl)-2-methyl-4-(2,6,6-trimethyl-1-cyclohexen-1-yl)-1,3-butadiene.

To a degassed (argon) solution of 0.2 g (3.4 mmol) of KOH in 1.5 mL of EtOH and 0.5 mL of water was added a solution of 0.293 g (0.82 mmol) of the ester of Example 5 in 1 mL of EtOH. The mixture was heated to 80° C. (bath temperature) over a 15-min period. After heating at 80° C. for 15 min, the pale-yellow solution was cooled to room temperature. The reaction mixture was quenched with 4 mL of 25% aqueous HOAc, diluted with 10 mL of water, and extracted with 10 mL of $Et_2O$. The $Et_2O$ solution was washed with water (2×5 mL), dried ($Na_2SO_4$), and concentrated. The yellow solid was recrystallized from 2 mL of MeOH under argon to give 0.211 g (78% yield) of yellow crystals of product acid, mp 141°–142° C.: LC (Radialpak A, 40% $H_2O$/MeCN, 2.0 mL/min, 280 nm) $t_R$ 2.1 min (100%); IR ($CHCl_3$) 3300–2300 (OH), 1690 (C=O), 1610, 1560, 1420, 1280, 1210, 1115, 1080, 965, 935, 895 cm$^{-1}$; 300 MHz $^1$H NMR ($CDCl_3$) δ 1.06 (s, 6, $16_R$, $17_R$ $CH_3$), 1.49 and 1.64 (2 m, 4, $2_R, 3_R$ $CH_2$), 1.75 (s, 3, $18_R$ $CH_3$), 2.04 (s, 3, $19_R$ $CH_3$), 2.04 (m, 2, $4_R$ $CH_2$), 6.26 (d, J=16 Hz, 1, $8_R$ HC=CH), 6.34 (d, J=16 Hz, 1, $7_R$ HC=CH), 6.47 (s, 1, $10_R$ C=CH), 7.44 (dd, J=8 Hz, J=8 Hz, 1, 6' H), 7.78 (dd, J=10.5 Hz, J=1 Hz, 1, 3' H), 7.88 (dd, J=8 Hz, J=1 Hz, 1, 5' H); $^{13}$C NMR ($CDCl_3$) 14.3 ($19_R$), 19.2 ($3_R$), 21.7 ($18_R$), 28.9 ($16_R$, $17_R$), 33.0 ($4_R$), 34.3 ($1_R$), 39.5 ($2_R$), 117.0 (d, J=24 Hz, 3'), 121.0 (5'), 125.4 (6'), 128.8 (d, J=8 Hz, 4'), 129.1 (10 $_R$), 129.9 ($5_R$), 130.7 ($7_R$), 131.9 (d, J=14 Hz, 1'), 137.3 and 137.4 ($6_R, 8_R$), 140.5 ($9_R$), 159.9 (d, J=148 Hz, 2'), 171.3 ppm (C=O); UV (EtOH) $\lambda_{max}$ 313 nm (ε 2.30×10$^4$); MS calcd for $C_{21}H_{25}FO_2$ 328.1838, found 328.1818.

The retinoids of formula (1) may be used topically or systemically as chemopreventive agents and in the treatment, amelioration, or prevention of the skin disorders and rheumatic disorders for which retinoic acid and other retinoids are useful. In this regard, they may be used for therapy in animals, including humans, of premalignant epithelial cell lesions, as a prophylaxis against tumor promotion in epithelial cells and treatment for dermatoses such as icthyoses, follicular disorders, benign epithelial disorders, and other proliferative skin diseases (non-malignant conditions of the skin that are characterized by epidermal cell proliferation or incomplete cell differentiation) such as acne, psoriasis, eczema, atopic dermatitis, nonspecific dermatitis and the like. When used for such treatments they will usually be formulated with a pharmaceutically liquid, semi-solid, or solid carrier. A pharmaceutically acceptable carrier is a material that is nontoxic and generally inert and does not affect the functionality of the active ingredients adversely. Such materials are well known and include those materials sometimes referred to as diluents or vehicles in the pharmaceutical formulation art. The carrier may be organic or inorganic in nature. Examples of pharmaceutically acceptable carriers that may be used to formulate the retinoids are water, gelatin, lactose, starch, mineral oil, cocoa butter, dextrose, sucrose, sorbitol, mannitol, gum acacia, alginates, cellulose, talc, magnesium stearate, polyoxyethylene sorbitan monolaurate, and other commonly used pharmaceutical carriers. In addition to the retinoid and carrier the formulation may contain minor amounts of additives such as flavoring agents, coloring agents, thickening or gelling agents, emulsifiers, wetting agents, buffers, stabilizers, and preservatives such as antioxidants.

For topical administration the retinoids are conveniently provided in the form of ointments, tinctures, creams, solutions, lotions, sprays, suspensions, and the like. The amount of retinoid in such topical formulations will normally be in the range of about 0.01 to about 1% by weight. For enteral (oral or rectal) administration the retinoids will typically be formulated as tablets, capsules, dragees, syrups, solutions, or suppositories. For parenteral administration the retinoids will be formulated as injectable solutions or suspensions.

The dosages and dosage regimen in which the retinoids are administered will vary according to, the dosage form, mode of administration, the condition being treated and particulars of the patient being treated. They will, of course, be administered in chemopreventive (tumor promotion inhibiting) amounts or therapeutically effective amounts. For adult humans such chemopreventive amounts will usually be about 0.01 mg to 10.0 mg daily given in one or more doses. Oral doses will generally be less that topical doses and doses for treating skin disorders will typically be less than doses administered for cancer chemoprevention. The dose for treating skin disorders will be on the order of, but normally less than, the dose of retinoic acid prescribed for the disorder.

The usefulness of the invention compounds was demonstrated by testing the compounds of the Examples in the ornithine decarboxylase (ODC) assay, Verma, A. K. and Boutwell, R. K., *Cancer Res* (1977) 37:2196–2201, and the tracheal organ culture assay, Newton, D. L.; Henderson, W. R.; and Sporn, M. B., *Cancer Res* (1980) 40:3413–3425. The ODC assay measures a compound's ability to prevent the induction of ODC. The tracheal organ culture assay measures a compound's ability to reverse keratinization.

The ODC assay is carried out as follows. Female Charles River CD-1 mice from Charles River Breeding Laboratories, Wilmington, Massachusetts, are used (age 7 to 9 weeks). The dorsal hair of the mice is shaved 1 to 2 days before testing, and only mice showing no hair regrowth are used. A single dose of 12-O-tetradecanoylphorbol-13-acetate (TPA) (10.5 µg, 17 nmol) in 0.2 mL of acetone is applied topically to the back of each mouse. The test compound, at one of three dose levels (1.7, 17 and 170 nmol), dissolved in 0.2 mL of acetone is applied 1 hour before the TPA treatment to the test groups; the control group is treated with acetone alone. The mice are killed by cervical dislocation five hours after TPA treatment. Determinations are done in triplicate.

The epidermis is obtained from the sacrificed animals. To obtain sufficient material, the dorsal skins from 2 to 3 mice in each treatment group are pooled. The depilatory agent Nudit ® (Helena Rubinstein, New York) is applied to the shaved area of the skin; after 5 minutes, it is washed off thoroughly with cold tap water. Then the skin is excised and plunged immediately into ice-cold water; it is then placed in a 55° C. water bath for 30 seconds and reimmersed in ice-cold water for at least another 30 seconds. The skin is placed epidermis side up on a cold plate, and the epidermis is scraped off with a razor blade. The pooled epidermal sheets are homogenized (Polytron PT-10 homogenizer) at 0° to 4° C. for 15–20 seconds in 50 mM sodium phosphate and 0.1 mM ethylenediaminetetraacetic acid (EDTA), at a volume of 1 mL/skin.

The supernatant fraction remaining after centrifugation of the homogenate at 10,000× g for 30 seconds at 0° C. is used for the enzyme assay. Enzyme activity is determined using the microassay for ODC as described by Verma and Boutwell to measure the release of $^{14}CO_2$ from DL-[1-$^{14}$C]-ornithine (58 mCi/mmol) after incubation with the 10,000× g supernatant. The incubations are carried out by decanting, with a Pasteur pipette, 100 µL of the supernatant containing 100 to 120 µg of protein into two or three 15-mL Corex tubes in a shaking water bath at 37° C. The assay mixture in the tubes consists of 50 µL of 100 mM sodium phosphate buffer (pH 7.2), 10 µL of 4 mM pyridoxal phosphate, 40 µL of 25 mM dithiothreitol, and 1 µL of 0.1 M EDTA. The center wells in the tubes are filled with 200 µL of a 2:1 solution (v/v) of ethanolamine:2-methoxyethanol. The reaction is started by adding 50 µL of substrate (0.5 µCi of DL-[1-$^{14}$C]-ornithine in 2 mM cold ornithine) at 1-minute intervals by injection to each of the stoppered tubes. Incubations are routinely carried out at 37° C. for 30 to 60 minutes. The reaction is stopped by addition of 0.5 ml of 2 M citric acid, and incubation is continued for an additional hour without heating to ensure complete absorption of $^{14}CO_2$.

Radioactivity is measured using a toluene-based scintillant (4 g of PPO and 50 mg of POPOP/L of toluene) in a Beckman LS-250 liquid scintillation counter. Enzyme activity is determined in triplicate and expressed as nanomoles of $CO_2$ released in 30 minutes per milligram of protein. Enzyme activity is linear for the protein concentration used. The protein concentrations of the epidermal extracts are determined by the Lowry procedure, using bovine serum albumin as the standard.

The tracheal organ culture assay is carried out as follows. Tracheas are taken from hamsters that are in very early stages of vitamin A deficiency and placed in organ culture. At the time of culture, the animals are still gaining weight; the tracheal epithelium is generally low columnar or cuboidal, with only occasional patches of squamous metaplasia. Each trachea is opened from the larynx to the carina along the membranous dorsal wall and cultured in a serum-free medium (CMRL-1066; with crystalline bovine insulin, 0.1 µg/ml; hydrocortisone hemisuccinate, 0.1 µg/ml; glutamine, 2 mM; penicillin, 100 units/ml; and streptomycin, 100 µg/ml, added). Cultures are gassed with 50% oxygen, 45% nitrogen, and 5% $CO_2$. The culture dishes are rocked at 35.5–36.0 degrees to allow the tracheas contact with both gas and medium. All tracheas are grown in medium containing no retinoid for the first 3 days. At the end of 3 days, some tracheas are harvested; almost all of these tracheas have significant squamous metaplasia, and approximately 60% have keratinized lesions. The remaining tracheas are then divided into different groups which are treated with either: (1) retinoid dissolved in dimethylsulfoxide (final concentration of DMSO in culture medium is never greater than 0.1%) or (2) an equivalent amount of DMSO alone. Culture medium is changed three times a week, and all of the remaining tracheas are harvested at the end of 10 days in culture. Tracheas are fixed in 10% buffered formalin and embedded in paraffin. Cross sections of five micrometers are made through the mid-portion, stained with hematoxylin and eosin, and then scored with a microscope for the presence of keratin and keratohyaline granules, both of which are found in approximately 90% of control cultures that received no retinoid for the entire 10 day culture period. Retinoids are scored as "inactive" if both keratin and keratohyaline granules are seen; they are scored as "active" if neither keratin nor keratohyaline granules are seen, or if keratohyaline granules alone are absent.

The table below gives the results of these tests.

|  | Reversal of Keratinization in Hamster Tracheal Organ Culture | | Inhibition of Induction of Ornithine Decarboxylase by 12-O—Tetradecanoylphorbol-13-acetate in Mouse Skin | |
|---|---|---|---|---|
|  | Conc (M) | Active/Total Cultures (%) | Dose (nmol) | % Inhibition of Control |
| Example 1 | $10^{-8}$ | 11/12 (92) | 17 | 82 |
|  | $10^{-9}$ | 10/12 (83) | 1.7 | 56 |
|  | $10^{-10}$ | 6/13 (46) |  |  |
| Example 2 | $10^{-8}$ | 13/13 (100) | 17 | 80 |
|  | $10^{-9}$ | 12/13 (92) | 1.7 | 70 |
|  | $10^{-10}$ | 5/13 (38) |  |  |
| Example 3 | $10^{-8}$ | 7/7 (100) | 17 | 39 |
|  | $10^{-9}$ | 5/7 (71) | 1.7 | 21 |
|  | $10^{-10}$ | 4/7 (57) |  |  |
| Example 5 | $10^{-8}$ | 6/6 (100) | 17 | 46 |
|  | $10^{-9}$ | 6/7 (86) | 1.7 | 8 |
|  | $10^{-10}$ | 4/7 (56) |  |  |
| Example 6 | $10^{-8}$ | 6/6 (100) | 17 | 78 |

| Reversal of Keratinization in Hamster Tracheal Organ Culture | | Inhibition of Induction of Ornithine Decarboxylase by 12-O—Tetradecanoyl- phorbol-13-acetate in Mouse Skin | |
|---|---|---|---|
| Conc (M) | Active/Total Cultures (%) | Dose (nmol) | % Inhibition of Control |
| $10^{-9}$ | 12/12 (100) | 1.7 | 37 |
| $10^{-10}$ | 3/11 (27) | | |

These results indicate that the retinoids of the invention posses biological activity that makes them useful as chemopreventive agents and therapeutic agents for treating nonmalignant skin disorders.

Modifications of the above described modes for carrying out the invention that are obvious to those of skill in the fields of organic chemistry, pharmaceuticals, and/or medicine are intended to be within the scope of the following claims.

We claim:

1. A compound of the formula:

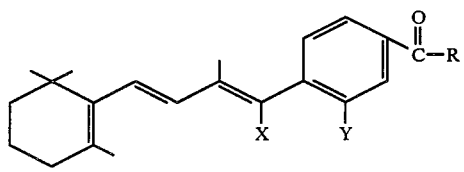

where X is H or F, Y is H, F, Cl, hydroxy, methyl, ethyl, methoxy or ethoxy, and R is hydroxyl, alkoxy, aroxy, or $NR^1R^2$ where $R^1$ is hydrogen, alkyl, or aryl and $R^2$ is alkyl or aryl, with the proviso that when Y is H, X is F.

2. The compound of claim 1 wherein the alkoxy group represented by R contains 1 to about 8 carbon atoms, the aroxy group represented by R contains 6 to about 15 carbon atoms, the alkyl groups represented by $R^1$ and $R^2$ each contain 1 to about 8 carbon atoms and have 0 to 1 hydroxy substituent, and the aryl groups represented by $R^1$ and $R^2$ each contain 6 to about 15 carbon atoms.

3. The compound of claim 1 wherein the alkoxy group represented by R contains 1 to 4 carbon atoms, the aroxy group represented by R is phenoxy, monohydroxyphenoxy, or monoalkoxyphenoxy where the alkoxy group contains 1 to 4 carbon atoms, the alkyl groups represented by $R^1$ and $R^2$ each contain 1 to 4 carbon atoms and have 0 or 1 hydroxy substituent, and the aryl groups represented by $R^2$ and $R^3$ are phenyl, 4-hydroxyphenyl, or 4-methoxyphenyl.

4. The compound of claim 1 where
 (a) R is ethoxy, X is fluorine, and Y is hydrogen; or
 (b) R is hydroxy, X is fluorine, and Y is hydrogen; or
 (c) R is ethoxy, X is hydrogen, and Y is methoxy; or
 (d) R is hydroxy, X is hydrogen and Y is methoxy; or
 (e) R is ethoxy, X is hydrogen, and Y is fluorine; or
 (f) R is hydroxy, X is hydrogen, and Y is fluorine.

5. A pharmaceutical composition comprising a pharmaceutically effective amount of the compound of claim 1 combined with a pharmaceutically acceptable carrier.

6. A chemopreventive composition for inhibiting tumor promotion in epithelial cells in a living animal comprising a tumor promotion inhibiting amount of the compound of claim 1 combined with a pharmaceutically acceptable carrier.

7. A therapeutic composition for treating a nonmalignant skin disorder comprising a therapeutically effective amount of the compound of claim 1 combined with a pharmaceutically acceptable carrier.

8. A method of inhibiting tumor promotion in epithelial cells of a living animal comprising administering a tumor promotion inhibiting amount of the compound of claim 1 to the animal.

9. The method of claim 8 where the animal is a human.

10. The method of claim 8 where the animal is a human and
 (a) R is ethoxy, X is fluorine, and Y is hydrogen, or
 (b) R is hydroxy, X is fluorine, and Y is hydrogen, or
 (c) R is ethoxy, X is hydrogen, and Y is methoxy, or
 (d) R is hydroxy, X is hydrogen, and Y is methoxy, or
 (e) R is ethoxy, X is hydrogen, and Y is fluorine, or
 (f) R is hydroxy, X is hydrogen, and Y is fluorine.

11. A method of treating a living animal for a nonmalignant skin disorder comprising administering a therapeutically effective amount of the compound of claim 1 to the animal.

12. The method of claim 11 where the animal is a human.

13. The method of claim 11 where the animal is a human and
 (a) R is ethoxy, X is fluorine, and Y is hydrogen, or
 (b) R is hydroxy, X is fluorine, and Y is hydrogen, or
 (c) R is ethoxy, X is hydrogen, and Y is methoxy, or
 (d) R is hydroxy, X is hydrogen, and Y is methoxy, or
 (e) R is ethoxy, X is hydrogen, and Y is fluorine, or
 (f) R is hydroxy, X is hydrogen, and Y is fluorine.

* * * * *